(12) United States Patent
Hsu et al.

(10) Patent No.: US 8,633,252 B2
(45) Date of Patent: Jan. 21, 2014

(54) USE OF PTEROSIN COMPOUNDS FOR TREATING DIABETES AND OBESITY

(75) Inventors: Feng-Lin Hsu, Taipei (TW); Shing-Hwa Liu, Taipei (TW); Biing-Jiun Uang, Hsinchu (TW)

(73) Assignees: Taipei Medical University, Taipei (TW); National Taiwan University, Taipei (TW); National Tsing Hua University, Taipei (TW); DCB-USA LLC, Wilmington, DE (US)

( * ) Notice: Subject to any disclaimer, the term of this patent is extended or adjusted under 35 U.S.C. 154(b) by 546 days.

(21) Appl. No.: 12/694,132

(22) Filed: Jan. 26, 2010

(65) Prior Publication Data

US 2010/0190732 A1 Jul. 29, 2010

Related U.S. Application Data

(60) Provisional application No. 61/147,382, filed on Jan. 26, 2009.

(51) Int. Cl.
*A61K 31/12* (2006.01)

(52) U.S. Cl.
USPC ............... 514/678; 514/25; 514/23; 514/729; 514/469

(58) Field of Classification Search
USPC .............................. 514/25, 23, 729, 681, 460
See application file for complete search history.

(56) References Cited

U.S. PATENT DOCUMENTS

| 2005/0152952 A1* | 7/2005 | Chokshi ........................ 424/439 |
| 2005/0153952 A1* | 7/2005 | Cho ........................... 514/210.02 |
| 2006/0111445 A1* | 5/2006 | Adje et al. .................... 514/567 |
| 2006/0188529 A1* | 8/2006 | Bobotas et al. ............... 424/400 |

FOREIGN PATENT DOCUMENTS

| EP | 0945438 A1 | 9/1999 |
| WO | WO 2006/082401 A1 | 8/2006 |

OTHER PUBLICATIONS

Serisier et al,. J. Nutr. 136:2037S-2040S, 2006.*
Castillo, et al., Isoptaquiloside and Caudatoside, Illudane-Type Sesquiterpene Glocosides From *Pteridium Aquilinum* Var. *Caudatum*, Phytochemisty, vol. 44, No. 5, pp. 901-906, 1997.

* cited by examiner

*Primary Examiner* — Brandon Fetterolf
*Assistant Examiner* — Jean Cornet
(74) *Attorney, Agent, or Firm* — Wolf, Greenfield & Sacks, P.C.

(57) ABSTRACT

This invention relates to the use of pterosin compounds of formula I for treating diabetes including type I and type II. Also disclosed is the use of the pterosin compounds for treating obesity.

18 Claims, 12 Drawing Sheets

A

B

A

B

USE OF PTEROSIN COMPOUNDS FOR TREATING DIABETES AND OBESITY

RELATED APPLICATION

This application claims priority to U.S. Provisional Application No. 61/147,382, filed on Jan. 26, 2009, the content of which is hereby incorporated by reference in its entirety.

BACKGROUND

Pterosin compounds are sesquiterpenoids existed in Bracken. Some members of this family are found to possess antineoplastic activity as previously described in, for example, Japan Pat. No. 63146839A2, *Chem. Pharm. Bull.* 1978, 26, 2346, *Molecules* 2008, 13, 255.

Diabetes, a disorder of sugar metabolism, is characterized by abnormally high blood glucose levels. There are two different types of diabetes, namely the non-insulin-dependent or maturity onset form, also known as type 2; and the insulin-dependent or juvenile onset form, also known as type 1.

Type 2 diabetes usually occurs in adults and is highly associated with obesity. Type 2 diabetic patients must control their diet and are encouraged to lose weight and to exercise. They take medicine that increase insulin sensitivity or stimulate the pancreas to release insulin. Current drugs for type 2 diabetes include sulfonylureas, meglitinides, biguanides, thiazolinediones, and α-glycosidase inhibitors, which however have a number of limitations, such as adverse effects and high rates of secondary failure. In contrast, type 1 diabetic patients are not over-weight relative to their age and height, and exhibit a rapid onset of the disease at an early age. Type 1 diabetic patients must administer insulin by injection for their entire life time. Although there has been much research on oral administration of insulin, no successful oral dosage of insulin is marketed at present.

As a result, there remains a need for alternative drugs for treatment of diabetes (type I and type II) and obesity which preferably have fewer advertise effects and can be orally administered.

SUMMARY

The present invention is based on the unexpected finding that a number of pterosin compounds possess anti-diabetic and anti-obesity activities.

Accordingly, in one aspect, this invention provides a method for treating diabetes (type I or type II) comprising administering to a subject in need of the treatment an effective amount of a pterosin compound of formula I:

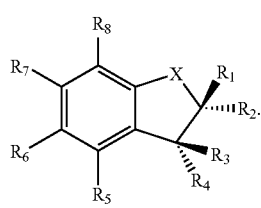

In formula I, each of $R_1$, $R_2$, $R_3$, and $R_4$, independently, is H, $OR_a$, amino, halogen, alkoxycarbonyl, alkylthio, alkylamino, alkyl, alkenyl, alkynyl, $-(G)_x$, $-O-(G)_x$ or $R_b-O-(G)_x$, $R_a$ being H, alkyl, alkenyl, alkynyl, cycloalkyl, heterocycloalkyl, aryl, or heteroaryl, $R_b$ being alkylene, alkenylene, alkynylene, cycloalkylene, heterocycloalkylene, arylene, or heteroarylene, G being a monosaccharide residue, and x being an integer of 1-4; each $R_5$, $R_6$, $R_7$, and $R_8$, independently, is H, $OR_c$, amino, nitro, cyano, halogen, alkoxycarbonyl, alkylthio, alkylamino, alkyl, alkenyl, alkynyl, aryl, heteroaryl, cycloalkyl, heterocycloalkyl, $-(G)_x$, $-O-(G)_x$, or $R_d-O-(G)_x$, $R_c$ being H, alkyl, alkenyl, alkynyl, cycloalkyl, heterocycloalkyl, aryl, or heteroaryl, $R_d$ being alkylene, alkenylene, alkynylene, cycloalkylene, heterocycloalkylene, arylene, or heteroarylene; or $R_5$, $R_6$, and the two carbon atoms to which they are attached, together form a 3-8 membered ring optionally containing 1, 2, or 3, heteroatoms; or $R_6$, $R_7$, and the two carbon atoms to which they are attached, together form a 3-8 membered ring optionally containing 1, 2, or 3, heteroatoms; or $R_7$, $R_8$, and the two carbon atoms to which they are attached, together form a 3-8 membered ring optionally containing 1, 2, or 3, heteroatoms; and X is C(O), C(S), S(O), CH(OH), C($R_e R_{e'}$), or C($NR_f$), each of $R_e$ and $R_{e'}$, independently, being H, alkyl, or cyano and $R_f$ being H, $OR_a$, amino, halogen, alkoxycarbonyl, alkylthio, alkylamino, alkyl, alkenyl or alkynyl.

Also within the scope of this invention is the use of any of the above-described pterosin compounds for treating diabetes and for the manufacture of a medicament for treating diabetes.

In another aspect, this invention provides a method for treating obesity comprising administering to a subject in need of the treatment an effective amount of a pterosin compound of formula I as described.

Also within the scope of this invention is the use of any of the pterosin compounds as described for treating obesity and for the manufacture of a medicament for treating obesity.

The details of one or more embodiments of the invention are set forth in the description below. Other features or advantages of the present invention will be apparent from the following detailed description of several embodiments, and also from the appended claims.

BRIEF DESCRIPTION OF THE SEVERAL VIEWS OF THE DRAWINGS

For the purpose of illustrating the invention, there are shown in the drawings embodiments which are presently preferred. It should be understood, however, that the invention is not limited to the preferred embodiments shown.

In the drawings.

DETAILED DESCRIPTION

Figure 1:
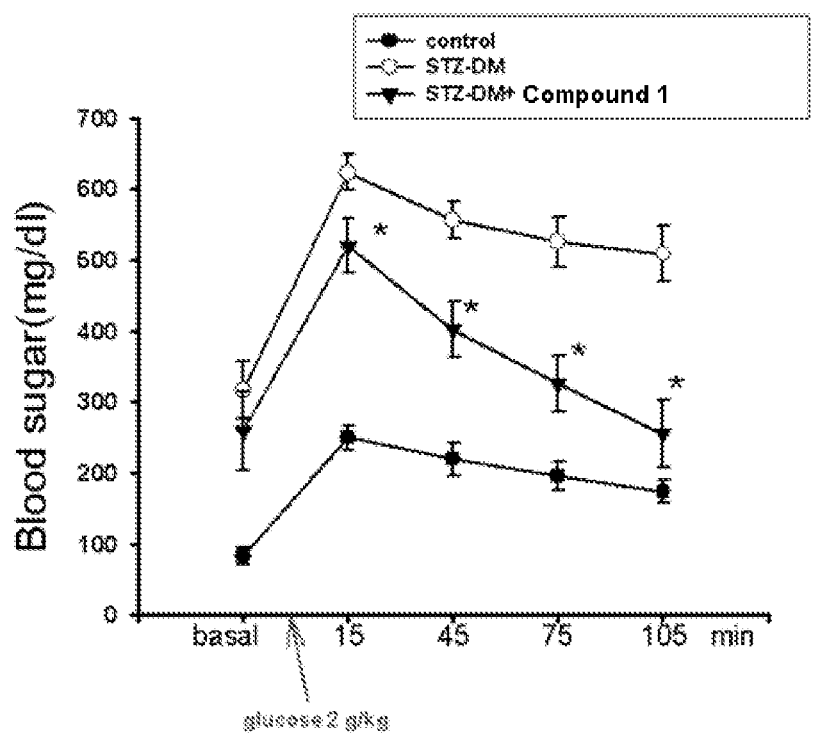
FIG. 1 shows the results of the glucose tolerance assay in streptozotocin (STZ)-induced diabetic mice treated with Compound 1 orally (100 mg/kg/day) for 14 days (Example 3). *p<0.05 represent statistical significance compared to the control.

Unless defined otherwise, all technical and scientific terms used herein have the same meaning as commonly understood by a person skilled in the art to which this invention belongs. All publications mentioned herein are incorporated herein by reference to disclose and describe the methods and/or materials in connection with which the publications are cited.

As used herein, the singular forms "a", "an", and "the" include plural referents unless the context clearly dictates otherwise. Thus, for example, reference to "a salt" includes a plurality of such salts and equivalents thereof known to those skilled in the art.

In one aspect, the present invention is directed to a method for treating diabetes comprising administering to a subject in need thereof an effective amount of a pterosin compound of formula I:

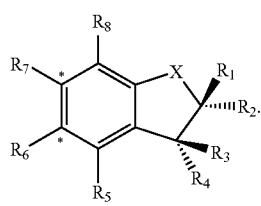

In formula I, each of $R_1$, $R_2$, $R_3$, and $R_4$, independently, is H, $OR_a$, amino, halogen, alkoxycarbonyl, alkylthio, alkylamino, alkyl, alkenyl, alkynyl, -(G)$_x$, —O-(G)$_x$ or $R_b$—O-(G)$_x$, $R_a$ being H, alkyl, alkenyl, alkynyl, cycloalkyl, heterocycloalkyl, aryl, or heteroaryl, $R_b$ being alkylene, alkenylene, alkynylene, cycloalkylene, heterocycloalkylene, arylene, or heteroarylene, G being a monosaccharide residue, and x being an integer of 1-4; each $R_5$, $R_6$, $R_7$, and $R_8$, independently, is H, $OR_c$, amino, nitro, cyano, halogen, alkoxycarbonyl, alkylthio, alkylamino, alkyl, alkenyl, alkynyl, aryl, heteroaryl, cycloalkyl, heterocycloalkyl, -(G)$_x$, —O-(G)$_x$, or $R_d$—O-(G)$_x$, $R_c$ being H, alkyl, alkenyl, alkynyl, cycloalkyl, heterocycloalkyl, aryl, or heteroaryl, $R_d$ being alkylene, alkenylene, alkynylene, cycloalkylene, heterocycloalkylene, arylene, or heteroarylene; or $R_5$, $R_6$, and the two carbon atoms to which they are attached, together form a 3-8 membered ring optionally containing 1, 2, or 3, heteroatoms; or $R_6$, $R_7$, and the two carbon atoms to which they are attached, together form a 3-8 membered ring optionally containing 1, 2, or 3, heteroatoms; or $R_7$, $R_8$, and the two carbon atoms to which they are attached, together form a 3-8 membered ring optionally containing 1, 2, or 3, heteroatoms; and X is C(O), C(S), S(O), CH(OH), C($R_e R_{e'}$), or C(NR$_f$), each of $R_e$ and $R_{e'}$, independently, being H, alkyl, or cyano and $R_f$ being H, $OR_a$, amino, halogen, alkoxycarbonyl, alkylthio, alkylamino, alkyl, alkenyl or alkynyl.

The term "alkyl" refers to a straight or branched monovalent hydrocarbon containing, unless otherwise stated, 1-20 carbon atoms (e.g., $C_1$-$C_8$). Examples of alkyl include, but are not limited to, methyl, ethyl, n-propyl, i-propyl, n-butyl, i-butyl, and t-butyl. The term "alkylene" refers to a straight or branched bivalent hydrocarbon, containing 1-20 carbon atoms (e.g., $C_1$-$C_8$). Examples of alkylene include, but are not limited to, methylene and ethylene. The term "alkenyl" refers to a straight or branched monovalent or bivalent hydrocarbon containing 2-20 carbon atoms (e.g., $C_2$-$C_{10}$) and one or more double bonds. Examples of alkenyl include, but are not limited to, ethenyl, propenyl, propenylene, allyl, and 1,4-butadienyl. The term "alkynyl" refers to a straight or branched monovalent or bivalent hydrocarbon containing 2-20 carbon atoms (e.g., $C_2$-$C_{10}$) and one or more triple bonds. Examples of alkynyl include, but are not limited to, ethynyl, ethynylene, 1-propynyl, 1- and 2-butynyl, and 1-methyl-2-butynyl. The term "alkoxycarbonyl" refers to an —O—C(O)—R radical in which R can be H, alkyl, alkenyl, alkynyl, cycloalkyl, cycloalkenyl, heterocycloalkyl, heterocycloalkenyl, aryl, or heteroaryl. The term "amino" refers to NH$_2$, alkylamino, or arylamino. The terms "alkylamino" and "alkylthio" refer to —N(R)-alkyl and —S(R)-alkyl radicals respectively, in which R can be H, alkyl, alkenyl, alkynyl, cycloalkyl, cycloalkenyl, heterocycloalkyl, heterocycloalkenyl, aryl, or heteroaryl. The term "amido" refers to an —NRC(O)R' radical, in which each of R and R', independently, can be H, alkyl, alkenyl, alkynyl, cycloalkyl, cycloalkenyl, heterocycloalkyl, heterocycloalkenyl, aryl, or heteroaryl.

The term "cycloalkyl" refers to a monovalent or bivalent saturated hydrocarbon ring system having 3 to 30 carbon atoms (e.g., $C_3$-$C_{12}$). Examples of cycloalkyl include, but are not limited to, cyclopropyl, cyclobutyl, cyclopentyl, cyclohexyl, 1,4-cyclohexylene, cycloheptyl, cyclooctyl, and adamantine. The term "heterocycloalkyl" refers to a monovalent or bivalent nonaromatic 5-8 membered monocyclic, 8-12 membered bicyclic, or 11-14 membered tricyclic ring system having one or more heteroatoms (such as O, N, S, or Se). Examples of heterocycloalkyl groups include, but are not limited to, piperazinyl, pyrrolidinyl, dioxanyl, morpholinyl, and tetrahydrofuranyl.

The term "aryl" refers to a monovalent 6-carbon monocyclic, 10-carbon bicyclic, 14-carbon tricyclic aromatic ring system. Examples of aryl groups include, but are not limited to, phenyl, naphthyl, and anthracenyl. The term "heteroaryl" refers to a monvalent aromatic 5-8 membered monocyclic, 8-12 membered bicyclic, or 11-14 membered tricyclic ring system having one or more heteroatoms (such as O, N, S, or Se). Examples of heteroaryl groups include pyridyl, furyl, imidazolyl, benzimidazolyl, pyrimidinyl, thienyl, quinolinyl, indolyl, and thiazolyl. The term "monosaccharide residue" used herein means a sugar which linked to together through glycosidic (ether) linkages and represent a structurally diverse class of biological molecules. The structural diversity of these compounds arises from the many different sugars and sugar derivatives such as glucuronic acids found in polysaccharides, not limited to a glucose residue and an arabinose, and each sugar can be covalently linked to other sugars through several different positions on the sugar ring. In addition, the glycosidic linkages can have either an cc or 13 configuration due to the stereochemistry of the sugars, and both types of linkages can exist in the same molecule.

Unless specifically pointed out, alkyl, alkenyl, alkynyl, alkoxycarbonyl, amino, alkylamino, alkylthio, cycloalkyl, heterocycloalkyl, aryl, and heteroaryl mentioned herein include both substituted and unsubstituted moieties. The term "substituted" refers to one or more substituents (which may be the same or different), each replacing a hydrogen atom. Examples of substituents include, but are not limited to, halogen (e.g. F, Cl, Br and I), hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cyclyoalkyl, and heterocyclyloalkyl, in which the alkyl, alkenyl, alkynyl, alkyloxy, aryl, heteroaryl, heteroaryloxy, alkylamino, arylamino, oxo (O=), thioxo (S=), thio, silyl, alkylthio, arylthio, alkylsulfonyl, arylsulfonyl, acylamino, aminoacyl, aminothioacyl, amidino, thioureido, thiocyanato, sulfonamido, guanidine, ureido, acyl, thioacyl, carbamyl (—C(O)NH$_2$), carboxyl (—COOH), and carboxylic ester in which alkyl, alkenyl, alkynyl, alkyloxycarbonyl, aryl, heteroaryl, cyclyl, and heterocyclyl may be further substituted. Cycloalkyl, cycloalkenyl, heterocycloalkyl, heterocycloalkenyl, aryl, and heteroaryl can also be fused with each other. Substituents may be protecting groups during the process of synthesis. The term "a protecting group" as used herein refers to a group or moiety, which is used to protect or mask a functionality during a process step in which it would otherwise react, but in which reaction is undesirable. The protecting group prevents reaction at that step, but may be subsequently removed to expose the original functionality. Examples of a protecting group include but are not limited to triethylsilyl (TES), tert-butyloxycarbonyl (tBoc), carbobenzyloxy (CBZ), and fluoren-9-ylmethoxycarbonyl (Fmoc).

The pterosin compounds described herein include the compounds themselves, as well as their salts, prodrugs, and solvates, if applicable. A salt, for example, can be formed between an anion and a positively charged group (e.g., amino) on a pterosin compound. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group (e.g., carboxylate) on a pterosin compound. Suitable cations include sodium ion, potassium ion, magnesium ion, calcium ion, and an ammonium cation such as tetramethylammonium ion. The pterosin compounds also include those salts containing quaternary nitrogen atoms. Examples of prodrugs include esters and other pharmaceutically acceptable compounds, which, upon administration to a subject, are capable of providing active pterosin compounds. A solvate refers to a complex formed between an active pterosin compound and a pharmaceutically acceptable solvent. Examples of pharmaceutically acceptable solvents include water, ethanol, isopropanol, ethyl acetate, acetic acid, and ethanolamine.

In one embodiment, X is C(O) or CH$_2$, and particularly C(O).

In another embodiment, each of $R_1$, $R_2$, $R_3$, and $R_4$, independently, is H, OR$_a$, -(G)$_x$, —O-(G)$_x$, R$_b$—O-(G)$_x$ or alkyl optionally substituted with halogen, COOR$_g$, OR$_g$, R$_g$ being H, alkyl, cycloalkyl, heterocycloalkyl, or a protecting group.

In still another embodiment, each of $R_5$, $R_6$, $R_7$, and $R_8$, independently, is H, OR$_c$, -(G)$_x$, —O-(G)$_x$, R$_d$—O-(G)$_x$, or alkyl optionally substituted with halogen, COOR$_g$, OR$_g$, R$_g$ being H, alkyl, cycloalkyl, heterocycloalkyl, or a protecting group.

Specifically, Table 1 shows exemplary pterosin compounds of formula I of the invention.

TABLE 1

| Compound | X | $R_1$ | $R_2$ | $R_3$ | $R_4$ | $R_5$ | $R_6$ | $R_7$ | $R_8$ |
|---|---|---|---|---|---|---|---|---|---|
| 1 | C=O | CH$_3$ | CH$_2$OH | H | H | H | CH$_3$ | CH$_2$CH$_2$OH | CH$_3$ |
| 2 | C=O | H | CH$_3$ | H | H | H | CH$_3$ | CH$_2$CH$_2$OH | CH$_3$ |
| 3 | C=O | CH$_3$ | H | H | H | H | CH$_3$ | CH$_2$CH$_2$OH | CH$_3$ |
| 4 | C=O | H | CH$_3$ | H | OH | H | CH$_3$ | CH$_2$CH$_2$OH | CH$_3$ |
| 5 | C=O | CH$_3$ | H | H | OH | H | CH$_3$ | CH$_2$CH$_2$OH | CH$_3$ |
| 6 | C=O | CH$_3$ | H | OH | H | H | CH$_3$ | CH$_2$CH$_2$OH | CH$_3$ |
| 7 | C=O | CH$_3$ | CH$_3$ | H | OH | H | CH$_3$ | CH$_2$CH$_2$OH | CH$_3$ |
| 8 | C=O | H | CH$_3$ | H | H | H | CH$_3$ | C2H$_4$COOH | CH$_3$ |
| 9 | C=O | H | CH$_3$ | H | H | H | CH$_3$ | CH$_2$CH$_2$Cl | CH$_3$ |
| 10 | C=O | H | CH$_2$OH | H | H | H | CH$_3$ | CH$_2$CH$_2$OH | CH$_3$ |
| 11 | C=O | CH$_3$ | CH$_3$ | H | H | H | CH$_3$ | CH$_2$CH$_2$Cl | CH$_3$ |
| 12 | C=O | CH$_3$ | CH$_3$ | H | H | H | CH$_3$ | CH$_2$CH$_2$OCH$_3$ | CH$_3$ |
| 13 | C=O | CH$_3$ | H | H | OH | H | CH$_3$ | CH$_2$CH$_2$Cl | CH$_3$ |
| 14 | C=O | CH$_3$ | CH$_2$OH | H | H | H | CH$_3$ | CH$_2$CH$_2$Cl | CH$_3$ |
| 15 | C=O | CH$_3$ | CH$_2$OH | H | OH | H | CH$_3$ | CH$_2$CH$_2$OH | CH$_3$ |
| 16 | C=O | CH$_3$ | CH$_2$OH | H | OH | H | CH$_3$ | CH$_2$CH$_2$OH | CH$_3$ |
| 17 | C=O | CH$_3$ | OH | H | H | H | CH$_3$ | CH$_2$CH$_2$OH | CH$_3$ |
| 18 | C=O | CH$_3$ | H | H | H | H | CH$_3$ | CH$_2$CH$_2$OCH$_3$ | CH$_3$ |
| 19 | C=O | H | CH$_3$ | H | H | H | CH$_3$ | CH$_2$CH$_2$OCH$_3$ | CH$_3$ |
| 20 | C=O | CH$_3$ | H | H | H | H | CH$_2$OH | CH$_2$CH$_2$OH | CH$_3$ |
| 21 | C=O | CH$_3$ | H | H | OH | H | CH$_3$ | CH(OH)CH$_2$OH | CH$_3$ |
| 22 | C=O | CH$_3$ | CH$_3$ | H | H | OH | CH$_3$ | CH$_2$CH$_2$Cl | CH$_3$ |
| 23 | C=O | CH$_3$ | H | H | OH | H | CH$_3$ | CH$_2$CH$_2$OH | CH$_2$OH |
| 24 | C=O | CH$_3$ | H | H | OH | H | CH$_2$OH | CH$_2$CH$_2$OH | CH$_2$OH |
| 25 | C=O | CH$_3$ | H | H | OH | H | CH$_2$OH | CH$_2$CH$_2$OH | CH$_2$OH |
| 26 | C=O | CH$_2$OH | CH$_3$ | H | H | H | CH$_3$ | CH$_2$CH$_2$OCH$_3$ | CH$_3$ |
| 27 | C=O | CH$_3$ | CH$_3$ | OH | H | H | CH$_3$ | CH$_2$CH$_2$OH | CH$_2$OH |

TABLE 1-continued

| Compound | X | R₁ | R₂ | R₃ | R₄ | R₅ | R₆ | R₇ | R₈ |
|---|---|---|---|---|---|---|---|---|---|
| 28 | C=O | $CH_3$ | $CH_3$ | H | OH | H | $CH_2OH$ | $CH_2CH_2OH$ | $CH_3$ |
| 29 | C=O | $CH_2OH$ | $CH_3$ | H | OH | H | $CH_2OH$ | $CH_2CH_2OH$ | $CH_3$ |
| 30 | C=O | $CH_3$ | $CH_3$ | H | H | H | $CH_3$ | $CH_2CH_2OH$ | $CH_3$ |
| 31 | C=O | $CH_3$ | $CH_2OH$ | H | H | H | $CH_3$ | $CH_2CH_2Oglu$ | $CH_3$ |
| 32 | C=O | $CH_3$ | $CH_2OH$ | H | H | H | $CH_3$ | $CH_2CH_2Oglu$ | $CH_3$ |
| 33 | C=O | $CH_3$ | $CH_2Oglu$ | H | H | H | $CH_3$ | $CH_2CH_2OH$ | $CH_3$ |
| 34 | C=O | H | $CH_3$ | H | H | H | $CH_3$ | $CH_2CH_2Oglu$ | $CH_3$ |
| 35 | C=O | $CH_3$ | H | H | H | H | $CH_3$ | $CH_2CH_2Oglu$ | $CH_3$ |
| 36 | C=O | H | $CH_3$ | OH | H | H | $CH_3$ | $CH_2CH_2Oglu$ | $CH_3$ |
| 37 | C=O | $CH_3$ | H | OH | H | H | $CH_3$ | $CH_2CH_2Oglu$ | $CH_3$ |
| 38 | C=O | $CH_3$ | H | H | OH | H | $CH_3$ | $CH_2CH_2Oglu$ | $CH_3$ |
| 39 | C=O | $CH_3$ | H | H | Oglu | H | $CH_3$ | $CH_2CH_2OH$ | $CH_3$ |
| 40 | C=O | $CH_3$ | H | Oglu | H | H | $CH_3$ | $CH_2CH_2Oglu$ | $CH_3$ |
| 41 | C=O | $CH_3$ | $CH_3$ | OH | H | H | $CH_3$ | $CH_2CH_2OH$ | H |
| 42 | C=O | $CH_3$ | $CH_3$ | H | Oglu | H | $CH_3$ | $CH_2CH_2OH$ | $CH_3$ |
| 43 | C=O | $CH_3$ | $CH_3$ | H | Oara | H | $CH_3$ | $CH_2CH_2Cl$ | $CH_3$ |
| 44 | C=O | $CH_3$ | $CH_2Oglu$ | H | H | H | $CH_3$ | $CH_2CH_2Oglu$ | $CH_3$ |
| 45 | C=O | $CH_3$ | $CH_2OH$ | H | OH | H | $CH_3$ | $CH_2CH_2Oglu$ | $CH_3$ |
| 46 | C=O | $CH_2OH$ | $CH_3$ | H | OH | H | $CH_3$ | $CH_2CH_2OH$ | $CH_3$ |
| 47 | C=O | $CH_3$ | $CH_2OH$ | H | Oara | H | $CH_3$ | $CH_2CH_2Oglu$ | H |
| 48 | C=O | H | $CH_3$ | H | Oglu | H | $CH_3$ | $CH_2CH_2Oglu$ | $CH_3$ |
| 49 | C=O | H | $CH_3$ | H | H | H | $CH_3$ | $CH_2CH_2OCH_3$ | $CH_3$ |
| 50 | C=O | $CH_3$ | H | H | H | H | $CH_2OH$ | $CH_2CH_2Oglu$ | $CH_3$ |
| 51 | C=O | $CH_3$ | H | H | H | OH | $CH_3$ | $CH_2CH_2Oglu$ | $CH_3$ |
| 52 | C=O | $CH_3$ | $CH_3$ | H | H | H | $CH_3$ | $CH_2CH_2Oglu$ | $CH_3$ |
| 53 | C=O | $CH_3$ | $CH_3$ | H | Oara | H | $CH_3$ | $CHOHCH_2OH$ | $CH_3$ |
| 54 | C=O | $CH_3$ | $CH_3$ | H | H | Oglu | $CH_3$ | $CH_2CH_2OH$ | $CH_3$ |
| 55 | C=O | $CH_3$ | $CH_3$ | H | OH | H | | δ-lactone ring | H |
| 56 | C=O | $CH_3$ | H | $CH_3$ | Oglu | H | $CH_3$ | $CH_2CH_2OH$ | $CH_3$ |
| 57 | C=O | $CH_3$ | H | H | H | OH | $CH_3$ | $CH_2CH_2OH$ | $CH_3$ |
| 58 | C=O | $CH_3$ | $CH_2OH$ | H | H | OH | $CH_3$ | $CH_2CH_2OH$ | $CH_3$ |
| 59 | C=O | $CH_3$ | $CH_2OH$ | H | OH | H | | δ-lactone ring | $CH_3$ |
| 60 | C=O | $CH_3$ | $CH_3$ | H | OH | H | $CH_3$ | $CH_2CH_2OCH_3$ | H |
| 61 | C=O | $CH_2OH$ | H | H | OH | H | $CH_3$ | $CH_2CH_2OH$ | H |
| 62 | C=O | $CH_2OH$ | H | H | OH | H | $CH_2OH$ | $CH_2CH_2OH$ | $CH_3$ |
| 63 | C=O | OH | $CH_3$ | H | OH | H | $CH_3$ | $CH_2CH_2OH$ | $CH_3$ |
| 64 | C=O | OH | $CH_3$ | H | OH | H | $CH_2OH$ | $CH_2CH_2OH$ | $CH_3$ |
| 65 | C=O | $CH_3$ | $CH_3$ | H | OH | H | $CH_3$ | $CH_2CH_2Cl$ | $CH_3$ |
| 66 | C=O | $CH_3$ | $CH_2OH$ | H | OH | H | $CH_3$ | $CH_2CH_2OH$ | $CH_2OH$ |
| 67 | $CH_2$ | $CH_3$ | H | H | H | $CH_3$ | $CH_2CH_2OH$ | $CH_3$ | H |
| 68 | C=O | $CH_3$ | H | H | H | H | $CH_2CH_2OH$ | $CH_3$ | H |
| 69 | C=O | $CH_3$ | $CH_3$ | H | OH | H | $CH_3$ | $CH_3$ | $CH_3$ |
| 70 | C=O | $CH_3$ | OH | H | H | H | $CH_3$ | $CH_3$ | $CH_3$ |
| 71 | C=O | $CH_3$ | $CH_3$ | H | H | H | $CH_3$ | $CH_2CH_2Oglu$ | $CH_3$ |
| 72 | C=O | $CH_3$ | $CH_3$ | H | 4cou-glu | H | $CH_3$ | $CH_2CH_2OH$ | $CH_3$ |
| 73 | C=O | $CH_3$ | $CH_3$ | 3glu | H | H | $CH_3$ | $CH_2CH_2OH$ | $CH_3$ |
| 74 | C=O | $CH_3$ | $CH_3$ | 6cou-glu | H | H | $CH_3$ | $CH_2CH_2OH$ | $CH_3$ |
| 75 | C=O | OH | $CH_3$ | H | OH | H | $CH_3$ | $CH_2CH_2OH$ | $CH_3$ |
| 76 | C=O | H | H | H | H | H | $CH_3$ | Br | $CH_3$ |
| 77 | C=O | COOEt | H | H | H | H | $CH_3$ | Br | $CH_3$ |
| 78 | C=O | COOEt | $CH_3$ | H | H | H | $CH_3$ | Br | $CH_3$ |
| 79 | C=O | COOEt | $CH_3$ | H | H | H | $CH_3$ | C≡C | $CH_3$ |
| 80 | COH | $CH_2OH$ | $CH_3$ | H | H | H | $CH_3$ | C≡C | $CH_3$ |
| 81 | COH | $CH_2OTES$ | $CH_3$ | H | H | H | $CH_3$ | C≡C | $CH_3$ |
| 82 | COH | $CH_2OTES$ | $CH_3$ | H | H | H | $CH_3$ | $CH_2CH_2OH$ | $CH_3$ |
| 83 | COH | $CH_2OTES$ | $CH_3$ | H | H | H | $CH_3$ | $CH_2CH_2TIPSO$ | $CH_3$ |
| 84 | C=O | $CH_2OTES$ | $CH_3$ | H | H | H | $CH_3$ | $CH_2CH_2TIPSO$ | $CH_3$ |

Compounds 76-84 refer to the synthetic compounds 3-11 as described in Example 1 below, respectively
glu: glucose; ara: arabinose
4cou-glu: 4-O-p-coumaroyl-D-glucose
3glu: 3-O-β-D-glucopyranoside
6cou-glu: 6-O-p-couumaroyl-D-glucose
*carbon is the same as that shown in formula.

More specifically, the pterosin compounds of formula I of the invention are Compound 1, 4, 5, 7, 10, 12, 15, 17, 28, 63 and 71-75.

Even more specifically, shown below are certain pterosin compounds of the invention with their structures:

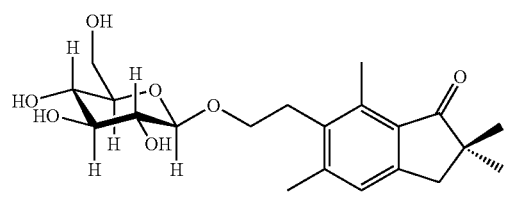

Pteroside Z(71)

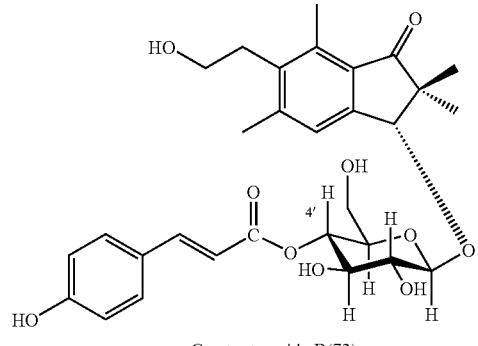

Ceratopteroside B(72)

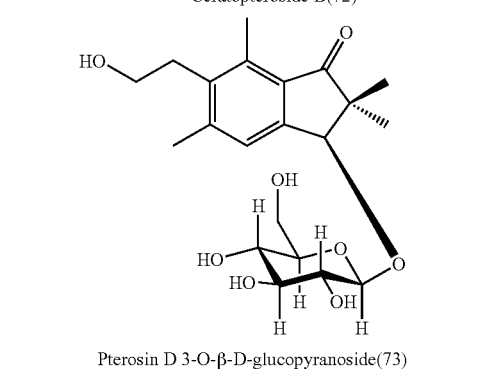

Pterosin D 3-O-β-D-glucopyranoside(73)

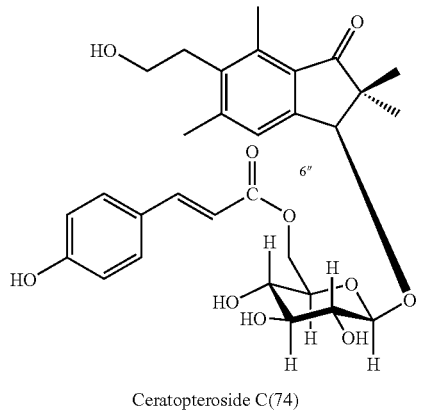

Ceratopteroside C(74)

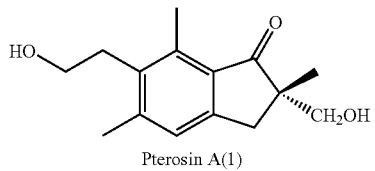

Pterosin A(1)

-continued

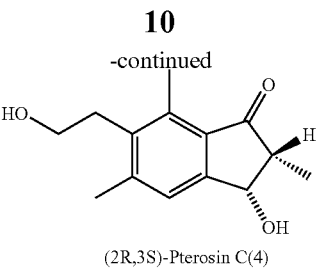

(2R,3S)-Pterosin C(4)

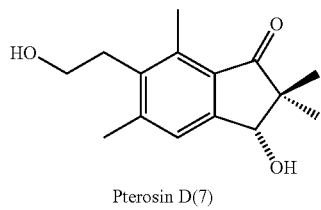

Pterosin D(7)

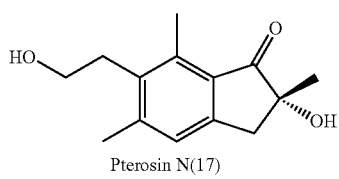

Pterosin N(17)

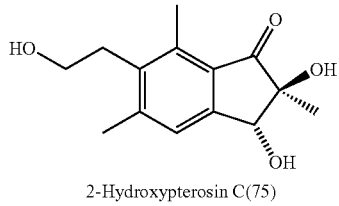

2-Hydroxypterosin C(75)

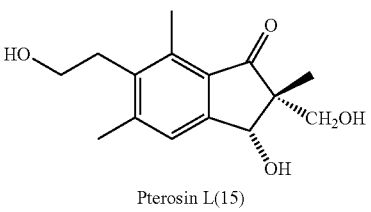

Pterosin L(15)

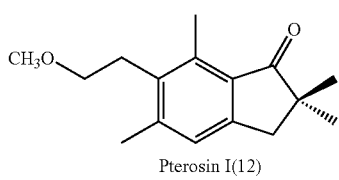

Pterosin I(12)

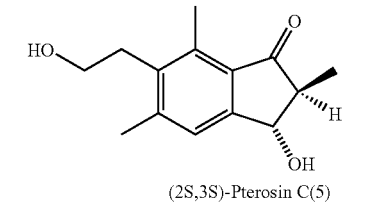

(2S,3S)-Pterosin C(5)

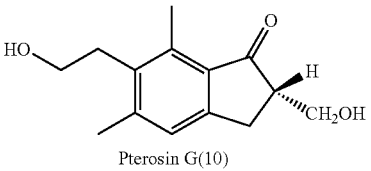

Pterosin G(10)

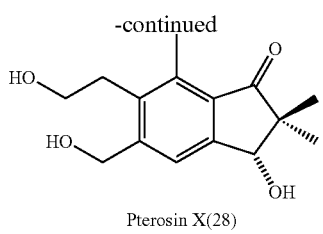

Pterosin X(28)

The pterosin compounds as used in this invention can be in an isolated form, i.e., prepared by a synthetic method or enriched from a natural source, e.g., Bracken, such as *Dennstaedtiaceae* and *Pteridaceae*. Certain examples of these plants include but are not limited to *Dennstaedtia scandens, Histiopteris incisa, Microlepia speluncae, Pteridium aquilinum* var. *latiusculum, Pteridium revolutum, Hypolepis punctata, Ceratopteris thalictroides, Pteris fauriei, Pteris dimidiata*, and *Pteris ensiformi*. These plants can be found in Wulai Township, Taipei County and Mountain Datun, Taipei City. For example, some of the pterosin compounds described herein (e.g., Compounds 1, 7, 28, and 71) are naturally occurring and therefore can be isolated from the natural sources. An isolated pterosin compound refers to a preparation that contains at least 40% of the compound by dry weight. Purity of an isolated compound can be measured by, e.g., column chromatography, mass spectrometry, high performance liquid chromatography (HPLC), NMR, or any other suitable methods.

Methods used for isolating these compounds are well known in the art. See, e.g., Takahashi et al., *Phytother. Res*, 2004, 18, 573, Sheridan et al., *Planta Med.*, 1999, 65, 271, Nagao et al., *Mutation Research*, 1989, 215, 173, Murakami et al., *Chem. Pharm. Bull*, 1976, 24, 2241, and Kuraishi et al., *Chem. Pharm. Bull*, 1985, 33, 2305. These compounds can also be made by chemical synthesis. Non-naturally occurring pterosin compounds can be either converted from those that are naturally-occurring (see, e.g., Banerji er al, *Tetrahedron Letters*, 1974, 15, 1369, Hayashi et al., *Tetrahedron Letters*, 1991, 33, 2509, and McMorris et al., *J. Org. Chem.*, 1992, 57, 6876), or synthesized de novo by methods well known in the art.

Synthetic chemistry transformations and protecting group methodologies (protection and deprotection) useful in synthesizing the desirable pterosin compounds are known in the art, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

A pterosin compound thus synthesized can be isolated from the reaction mixture with a suitable solvent, and optionally, further purified by flash column chromatography, high performance liquid chromatography, crystallization, or any other suitable methods.

The pterosin compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

The pterosin compounds of the invention can also be present in a fern product prepared from Bracken such as *Dennstaedtiaceae* and *Pteridaceae*. Certain examples of these plants include but not limited to *Dennstaedtia scandens, Histiopteris incisa, Microlepia speluncae, Pteridium aquilinum* var. *latiusculum, Pteridium revolutum, Hypolepis punctata, Ceratopteris thalictroides, Pteris fauriei, Pteris dimidiata*, and *Pteris ensiformis*. The fern product as described herein refers to any product from at least one of the plant of the above-identified species per se, its part(s), such as leaves, flowers, roots, seeds, stems and fruits, or any modified forms thereof such as juice, powders, granules, extracts, slices, concentrates, and precipitates. Specifically, the fern product is from the fresh whole plant.

A fern product of Bracken as described herein can be prepared by any standard method or techniques commonly known in the art. One example of the preparation of the fern extraction according to the invention is described below.

Preparation of the Fern Extraction

Column chromatography can be carried out with Diaion HP 20 (100-200 mesh, Mitsubishi Chemical Industries), MCI-gel CHP 20P (75-150 Mitsubishi Chemical Industries), Cosmosil C18-OPN (75 μm, Nacalai Tesque, Inc.), TLC (thin layer chromatography) on silica gel plates (60 F-254, Merk), and 10% sulfuric acid solution used as visualizing agent on heating. Fresh whole plants are extracted with methanol (×3, each 2 days) at room temperature. After evaporating the solvents in vacuo at 45° C., a residue is obtained. This residue is dissolved in distilled water and then extracted successively with n-hexane and ethyl acetate to provide a n-hexane soluble fraction, an ethyl acetate soluble fraction and a water soluble fraction. The organic soluble fraction is subjected to polydextran gel (Sephadex LH-20), high-porous polystyrene gel (Diaion HP-20, MCI CHP-20P) gel column chromatography (CC) eluting with water-methanol, ethanol or purified by silica gel CC with n-hexane, benzene, dichloromethane and methanol solvent system. The structures of purified compound can be confirmed by nuclear magnetic resonance (NMR) and mass spectrum (MS) spectra analyses and physical data.

According to the invention, the pterosin compounds of formula I are effective in treating diabetes including type I and type II.

As used herein, the term "type I diabetes", "juvenile onset diabetes" or "insulin-dependent diabetes" refer to the disease characterized by the pancreas making too little or no insulin. Patients afflicted with type I diabetes depend on insulin for survival; namely without insulin, the patients develop sever metabolic complications, such as acute ketoacidosis and coma.

As used herein, the term "type II diabetes", "maturity onset diabetes" or "non-insulin-dependent diabetes" refers to the disease characterized by excess glucose production in spite of the availability of insulin, and circulating glucose levels remain excessively high as a result of inadequate glucose clearance.

A "subject" is particularly a mammal, such as a human, but can also be a companion animal (e.g., dogs, cats, and the like), farm animals (e.g., cows, sheep, pigs, horses, and the like) or laboratory animals (e.g., rats, mice, guinea pigs, and the like) in need of the treatment as described. In one embodiment, the subject is obese.

The term "treating" includes prophylaxis of the specific disorder or condition, or alleviation of the symptoms associated with a specific disorder or condition and/or preventing or eliminating said symptoms. For example, as used herein the term "treating diabetes" will refer in general to reducing glucose levels, improving insulin sensitivity, or increasing glucose consumption.

"An effective amount" as used herein refers to the amount of each active agent required to confer therapeutic effect on the subject, either alone or in combination with one or more other active agents. Effective amounts vary, as recognized by those skilled in the art, depending on route of administration, excipient usage, and co-usage with other active agents. In one embodiment of the invention, the peterosin compounds are orally administered in an amount from 10 to 250 mg/kg, specifically 25 to 200 mg/kg, more specifically 50 to 150 mg/kg, and most specifically about 100 mg/kg. In another embodiment of the invention, the peterosin compounds are administered via subcutaneous injection, intraperitoneal injection, intramuscular injection or intravenous injection in an amount from 5 to 150 mg/kg, specifically 10 to 100 mg/kg, more specifically 20 to 80 mg/kg, and most specifically about 30 mg/kg.

To practice the above-noted treatment, one or more of the peterosin compounds described herein can be can be mixed with a pharmaceutically acceptable carrier to form a pharmaceutical composition. "Acceptable" means that the carrier must be compatible with the active ingredient of the composition (and preferably, capable of stabilizing the active ingredient) and not deleterious to the subject to be treated. Solubilizing agents, such as cyclodextrins (which form specific, more soluble complexes with one or more of active compounds of the extract), can be utilized as pharmaceutical excipients for delivery of the active compounds. Examples of other carriers include colloidal silicon dioxide, magnesium stearate, cellulose, sodium lauryl sulfate, and D&C Yellow #10.

The pharmaceutical composition can be administered orally, parenterally, by inhalation spray, or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A sterile injectable composition (e.g., aqueous or oleaginous suspension) can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents.

An oral composition can be any orally acceptable dosage form including, but not limited to, tablets, capsules, emulsions and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

An inhalation composition can be prepared according to techniques well known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

The present invention is also based on the unexpected finding that the pterosin compounds of formula I as described exhibit anti-obesity activities.

Therefore, the present invention further provides a method for treating obesity, comprising administering to a subject in need thereof an effective amount of a pterosin compound of formula I according to the invention.

Specifically, the method of the invention may reduce the serum lipid (e.g. triglycerides) or cholesterol levels in a subject.

Suitable in vitro assays can be used to preliminarily evaluate the efficacy of a pterosin compound in treating diabetes and obesity. The compound can further be examined for its efficacy in treating diabetes and obesity in vivo. For example, the compound can be administered to an animal having diabetes or obesity (e.g., an animal model induced by a chemical, genetic mutation or high fat food to develop diabetes or obesity) and its therapeutic effects are then accessed. Based on the results, an appropriate dosage range and administration route can also be determined.

Without further elaboration, it is believed that the above description has adequately enabled the present invention. The following specific example is, therefore, to be construed as merely illustrative, and not limitative of the remainder of the disclosure in any way whatsoever. All of the publications, including patents, cited herein are hereby incorporated by reference in their entireties.

Example 1

Synthesis of Compound 1

1.1 6-Bromo-5,7-dimethyl-1-indanone (3)

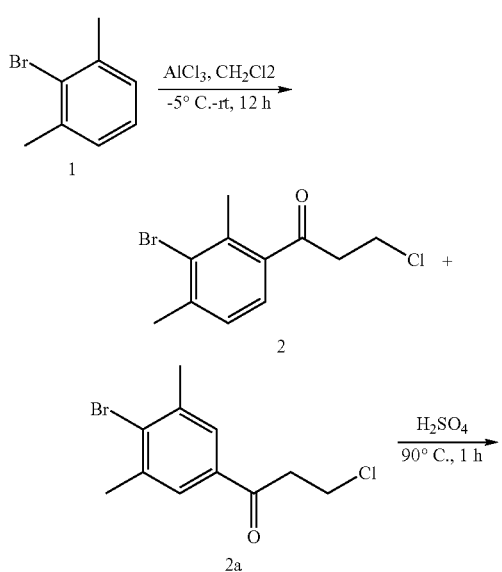

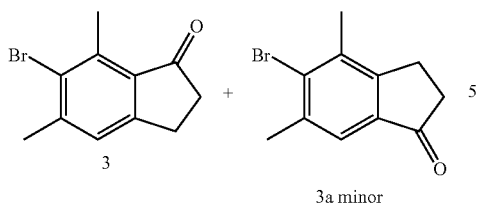

To the stirred solution of AlCl$_3$ (20.2 g, 151.3 mmol) and 3-Chloro-propionyl chloride (16.5 g, 129.7 mmol) in CH$_2$Cl$_2$ (80 mL), Bromoxylene (20.0 g, 108.1 mmol) with 40 mL CH$_2$Cl$_2$ in addition funnel was added drop wise at 0° C. The reaction mixture was warmed to room temperature and stirred for another 12 h. The reaction mixture was quenched with ice (200 g) and 50 mL HCl (neat) and allowed to stir for 15 min. Then crude reaction mixture was extracted with ethyl acetate (300 mL×2 mL), washed with water (400 mL), brine (500 mL) dried (Na$_2$SO$_4$) and concentrated in vacuo.

Then the crude compound was added neat H$_2$SO$_4$ (165 mL) and stirred at 90° C. for 1 hr. After the reaction mixture was back to room temperature, quenched with ice (400 g). Crude reaction mixture was extracted with ethyl acetate (400 mL×2 mL), washed with water (500 mL), brine (500 mL) dried (Na$_2$SO$_4$) and concentrated in vacuo. The crude product was purified by silica gel column chromatography (hexanes/ethyl acetate, 12:1, v/v) gave pure compound 3 (10.1 g, 39.1%) as solid.

1.2 6-Bromo-5,7-dimethyl-1-oxo-indan-2-carboxylic acid ethyl ester (4)

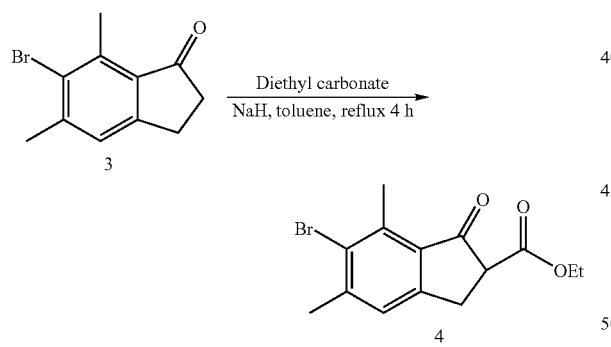

A 60% dispersion of sodium hydride (3.01 g, 125.5 mmol) in toluene (100 mL) added diethyl carbonate (30.5 mL, 251.04 mmol) the resulting solution mechanically stirred and refluxed. 1-indanone (10.0 g, 41.8 mmol) in toluene (50 mL) was added slowly to the refluxing solution over 3 hours. The addition funnel was washed with benzene (20 mL) and the reaction mixture refluxed for an additional 0.5 hours. The reaction mixture was added slowly into saturated aqueous NH$_4$Cl. The aqueous layer was extracted three times with ethyl acetate and the combined ethyl acetate extracts were washed with water, dried (Na$_2$SO$_4$), and the solvent removed in vacuo. The crude product was purified by silica gel column chromatography (hexanes/ethyl acetate, 15:1, v/v) gave pure compound 4 (11.5 g, 88.4%) as solid.

1.3 6-Bromo-2,5,7-trimethyl-1-oxo-indan-2-carboxylic acid ethyl ester (5)

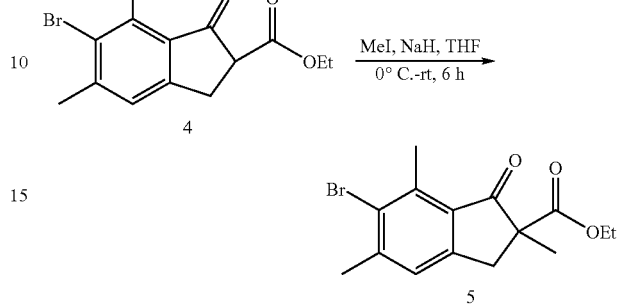

To the stirred solution of compound 4 (5.0 g, 16.1 mmol) in dry THF (50 mL), A 60% dispersion of sodium hydride (0.85 g, 35.4 mmol) in solid addition funnel was added portion wise at 0° C. The reaction mixture was warmed to room temperature and stirred for another 1 h. Then MeI (2.0 mL, 32.15 mmol) was added dropwise at 0° C. under argon atmosphere. The reaction mixture was warmed to room temperature and stirred for 5 h. The reaction mixture was quenched with saturated aqueous NH$_4$Cl solution at 0° C. and allowed to stir for 15 min. Then crude reaction mixture was extracted with ethyl acetate (100 mL×2 mL), washed with water (100 mL), brine (100 mL) dried (Na$_2$SO$_4$) and concentrated in vacuo. Purification by silica gel column chromatography (hexanes/ethyl acetate, 15:1, v/v) gave pure compound 5 (4.5 g, 86.5%).

1.4 2,5,7-Trimethyl-1-oxo-6-vinyl-indan-2-carboxylic acid ethyl ester (6)

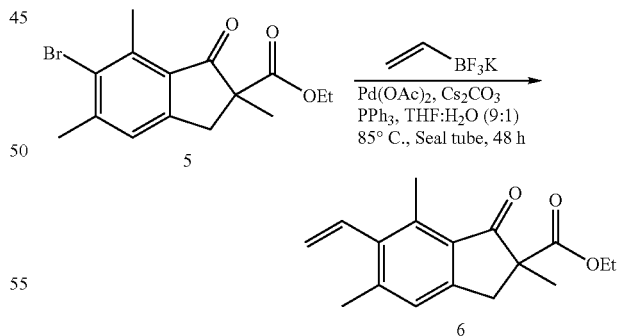

A solution of potassium vinyltrifluoroborate (0.186 g, 1.38 mmol), PdCl$_2$, (0.033 g, 0.18 mmol), PPh$_3$ (0.073 g, 0.27 mmol), Cs$_2$CO$_3$ (1.2 g, 3.69 mmol) and compound 5 (0.3 g, 0.92 mmol) in THF/H$_2$O (9:1) (3 mL) was heated at 85° C. under an Argon atmosphere in a sealed tube. The reaction mixture was stirred at 85° C. for 48 h, then cooled to room temperature and diluted with H$_2$O (6 mL) followed by extraction with ethyl acetate (30 mL), dried (Na$_2$SO$_4$) and concentrated in vacuo. Purification by column chromatography (SiO₂, 2 to 4% EtOAc in petroleum ether eluant) gave pure compound 6 (0.23 g, 92%).

1.5 2-Hydroxymethyl-2,5,7-trimethyl-6-vinyl-indan-1-ol (7)

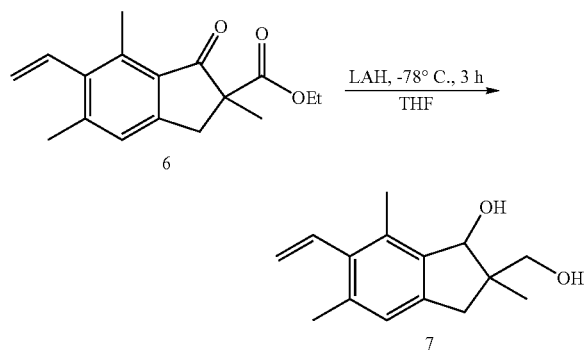

To the stirred solution of compound 6 (1.3 g, 4.77 mmol) in dry THF (10 mL) was added LAH (0.212 g, 5.73 mmol) at −78° C. under argon atmosphere and stirred the reaction mixture for 3 h then the reaction mixture was warmed to 0° C. and quenched with ethyl acetate (30 mL) at 0° C. After the reaction mixture was back to room temperature, extracted with 2M potassium sodium tartrate solution, washed with, brine (20 mL) dried (Na₂SO₄) and concentrated in vacuo. Purification by column chromatography (SiO₂, 15 to 20% EtOAc in petroleum ether eluant) gave pure compound 7 (0.88 g, 80%) as gummy syrup.

1.6 2,5,7-Trimethyl-2-triethylsilanyloxymethyl-6-vinyl-indan-1-ol (8)

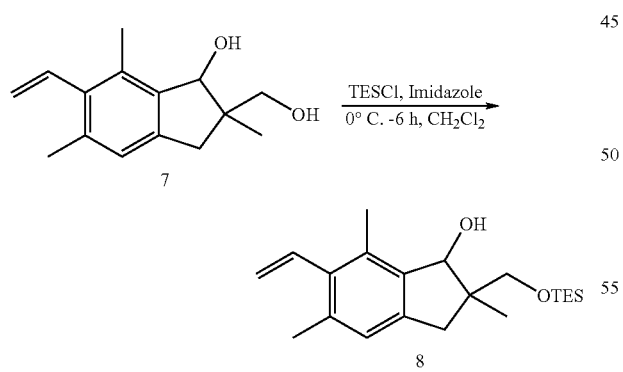

To the stirred solution of starting material 7 (0.85 g, 3.66 mmol) in dry CH₂Cl₂ added Imidazole (0.5 g, 7.32 mmol) and TESCl (0.6 mL, 3.66 mmol) sequentially at 0° C. under argon atmosphere and stirred the reaction mixture at same temperature for 6 h. Then reaction mixture was diluted with H₂O (10 mL) followed by extraction with CH₂Cl₂ (50 mL), brine (25 mL), dried (Na₂SO₄) and concentrated in vacuo. Purification by column chromatography (SiO₂, 5 to 10% EtOAc in petroleum ether eluant) gave pure compound 8 (0.85 g, 88%) as syrup.

1.7 6-(2-Hydroxy-ethyl)-2,5,7-trimethyl-2-triethylsilanyloxymethyl-indan-1-ol (9)

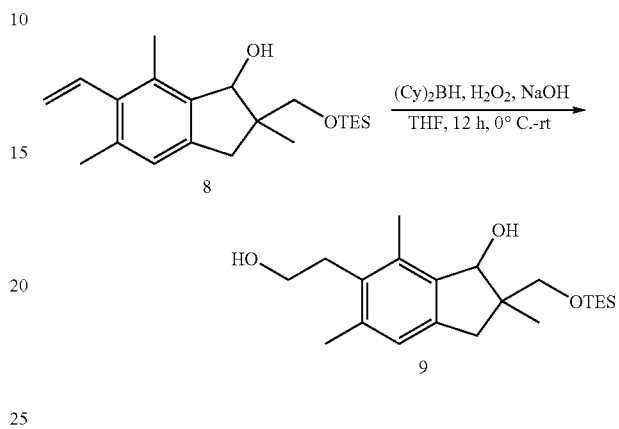

To the stirred solution of compound 8 (0.85 g, 2.45 mmol) in dry THF was added (Cy)₂BH (0.87 g, 4.91 mmol) slowly at 0° C. under argon atmosphere. The reaction mixture was warmed to room temperature and stirred for 12 h. The reaction mixture was quenched with 2N NaOH (6 mL) and H₂O₂ (3 mL) at 0° C. and allowed to stir for 4 h. Then crude reaction mixture was extracted with ethyl acetate (40 mL), washed with water (10 mL), brine (10 mL) dried (Na₂SO₄) and concentrated in vacuo. Purification by column chromatography (SiO₂, 8 to 10% EtOAc in petroleum ether eluant) gave pure compound 9 (0.72 g, 81%) as gummy syrup.

1.8 2,5,7-Trimethyl-2-triethylsilanyloxymethyl-6-(2-triisopropylsilanyl oxy-ethyl)-indan-1-ol (10)

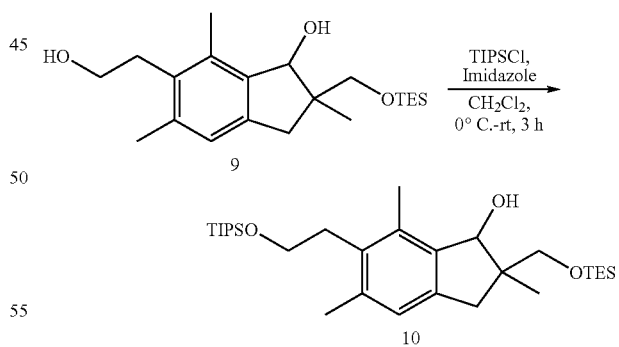

To the stirred solution of starting material 9 (0.7 g, 1.92 mmol) in dry CH₂Cl₂ added imidazole (0.262 g, 3.84 mmol) and TIPSCl (0.45 mL, 2.11 mmol) sequentially at 0° C. under argon atmosphere. The reaction mixture was warmed to room temperature and stirred for 3 h at room temperature. Then reaction mixture was diluted with H₂O (10 mL) followed by extraction with CH₂Cl₂ (30 mL), brine (10 mL), dried (Na₂SO₄) and concentrated in vacuo. Purification by column chromatography (SiO$_2$, 2 to 4% EtOAc in petroleum ether eluant) gave pure compound 10 (0.82 g, 82%).

1.9 2,5,7-Trimethyl-2-triethylsilanyloxymethyl-6-(2-triisopropyl silanyloxy-ethyl)-indan-1-one (11)

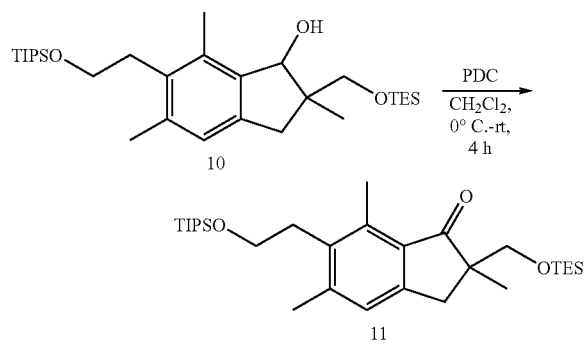

To the stirred solution of compound 10 (0.8 g, 1.54 mmol) in dry CH$_2$Cl$_2$ was added PDC (1.15 g, 3.07 mmol) at 0° C. under argon atmosphere. The reaction mixture was warmed to room temperature and stirred for 4 h at room temperature. The reaction mixture was concentrated in vacuo. The crude product was purified by column chromatography (SiO$_2$, 1 to 3% EtOAc in petroleum ether eluant) gave pure compound 9 (0.64 g, 81%) as a colorless syrup.

1.10 6-(2-Hydroxy-ethyl)-2-hydroxymethyl-2,5,7-trimethyl-indan-1-one (12)

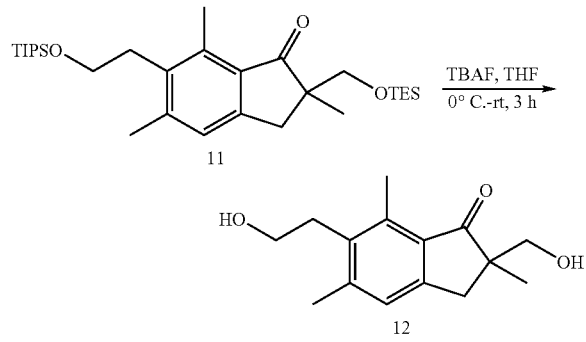

To the stirred solution of compound 1I (0.64 g, 1.23 mmol) in dry THF was added tetra n-butyl ammonium fluoride in THF (0.65 g, 2.47 mmol) at 0° C. and stirred at room temperature for 3 h. Then reaction mixture was diluted with H$_2$O (10 mL) followed by extraction with ethyl acetate (30 mL), brine (10 mL), dried (Na$_2$SO$_4$) and concentrated in vacuo. Purification by column chromatography (SiO$_2$, 15 to 20% EtOAc in petroleum ether eluant) gave pure compound 12 (0.26 g, 85%).

Example 2

Plant Extraction 2.1 *Hypolepis punctata* (Thunb.) Mett
*Hypolepis punctata* (Thunb.) Mett. was collected from Wulai Township, Taipei County. Fresh whole plant (11 kg) of *Hypolepis punctata* was extracted with MeOH (20 L) thee times at room temperature to yield a MeOH extract, which was partitioned between n-hexane-H$_2$O (1:1) (1.5 L×3) to provide a n-hexane soluble fraction and a H$_2$O soluble fraction. The H$_2$O soluble fraction was partitioned between EtOAc—H$_2$O (1:1) (1.5 L×3) to provide an EtOAc soluble fraction and a H$_2$O soluble fraction. The EtOAc soluble fraction was subjected to Diaion HP-20 gel column chromatography (CC) eluting with H$_2$O, gradually increasing the MeOH to furnish fractions 1-4. Fraction 2 was applied to Sephadex LH-20 CC eluting with 95% EtOH to afford fractions 2-1-2-2. Fraction 2-1 was purified by Sephadex LH-20 CC (H$_2$O→MeOH) to obtain fraction 2-1-1~2-1-3. Purify fraction 2-1-2 by MCI gel CHP-20P CC(H$_2$O→MeOH), pterosin A (128 mg) was obtained. Fraction 3 was subjected to silica gel CC, eluting gradually with CH$_2$Cl$_2$ and MeOH to give 3-1~3-5 fractions. Fraction 3-2 was applied to silica gel CC, developed with CH$_2$Cl$_2$-MeOH (9:1) to obtain pterosin Z (790 mg). Fraction 3-4 was subjected to silica gel CC, eluting with EtOAc-n-Hexane (4:1) to give pterosin I (24 mg). Fraction 4 was applied to Sephadex LH-20 gel CC eluting with MeOH to afford 2 fractions. Frection 4-1 was purified by MCI CHP-20P gel CC(H$_2$O→MeOH) and Silica gel CC with EtOA-n-Hexane (7:3) to obtain pterosin D (20 mg).

2.2 *Pteridium revotulum* (BI.) Nakai
*Pteridium revotulum* (BI.) Nakai was collected from Mt. Datun, Taipei City. At room temperature, fresh whole plant of *Pteridium revotulum* (BI.) Nakai (20 kg) was extracted with MeOH (20 L×3) to yield a MeOH extract, after evaporate organic solvent the extract was subjected to Celite CC sequent elute with n-hexane, CH$_2$Cl$_2$ and MeOH to afford 3 fractions. The CH$_2$Cl$_2$ soluble fraction was subjected to MCI CHP-20P gel CC eluting with H$_2$O and MeOH (1:1→0:1) to furnish 3 fractions. Fraction 1 was purified by silica gel CC and eluting with CH$_2$Cl$_2$ and MeOH (14:1) to give fractions 1-1~1-3. Fraction 1-1 was applied to silica gel CC (n-hexane-EtOAc=1:2) and ODS gel CC(CH$_3$CN—H$_2$O=20:80→30:70) to afford (2S)-pterosin A (238 mg), (3R)-pterosin D (38 mg), (2R)-pterosin N (21 mg), (2R,3R)-pterosin L (179 mg) and (2R)-pterosin G (73 mg). Fraction 1-2 was purified by silica gel CC eluting with n-hexane-EtOAc (1:2) and ODS gel CC with CH$_3$CN: H$_2$O (1:9) to produce (3R)-pterosin X (2.2 mg) and (2)-hydroxypterosin C (4.3 mg). Fraction 2 was applied to silica gel CC (n-hexane-EtOAc=1:2) and HPLC-silica (10 n-hexane-EtOAc=2:1→1:2) to afford (2S,3S)-pterosin C (162 mg) and (2R,3S)-pterosin C (13 mg).

2.3 Other Species
The whole plants of other species of Bracken including *Dennstaedtia scandens, Histiopteris incisa, Microlepia speluncae, Pteridium aquilinum* var. *latiusculum, Ceratopteris thalictroides, Pteris fauriei, Pteris dimidiata*, and *Pteris ensiformis* were extracted as above and confirmed to contain at least pterosin A, pterosin I and pterosin Z (data not shown).

Example 3

Glucose Tolerance Assay in Type I Diabetic Mice

Streptozotocin (STZ)-induced diabetic mice were administered orally with Compound 1 (50 mg/kg). STZ-induced diabetic mice are a well-known mouse model of type I diabetes (insulin dependent). See, e.g., Liu I M, et al., *Neuroscience Letters* 2001; 307: 81-84.

Two hours later, normal mice, STZ-induced diabetic mice, and the Compound 1-treated STZ-mice as described were subjected to a glucose tolerance assay. Briefly, all of the mice were orally administered with 1 g/kg glucose and the blood glucose levels of these mice were examined at 30, 60, 90, 120 and 150 minutes. In the normal and STZ-diabetic mice, the blood glucose levels elevated 30 minutes after uptake of glucose. Surprisingly, in Compound 1-treated STZ-diabetic mice, the blood glucose levels were increased only slightly at 30 minute after glucose uptake and were significantly lowered 60 minutes after glucose uptake.

Alternatively, STZ-induced diabetic mice were treated with Compound 1 orally (100 mg/kg) for 14 days. These mice were then orally administered with glucose at a dose of 2 g/kg. Their blood glucose levels were examined 15, 45, 75, and 105 minutes after glucose administration. FIG. 1 shows the results.

Results thus obtained indicate that the blood glucose levels in health control mice, STZ-induced diabetic mice, and Compound 1 treated STZ-induced diabetic mice were increased 15 minutes after glucose administration. The blood glucose levels remained high in STZ-induced diabetic mice during the examined time period, while they decreased significantly in Compound 1-treated STZ-induced diabetic mice 45 minutes after glucose administration. The blood glucose levels in these treated mice were close to those of health control mice. Accordingly, the results described herein indicate that Compound 1 significantly lowered blood glucose levels in STZ-induced diabetic mice. Other pterosin compounds of the invention as listed in Table 1 including Compounds 7, 72, 73, 74 were also demonstrated to have the same effect in this assay.

Specifically, no advertise effects e.g. abnormal results from blood assays and pathological evaluation were observed in the mice after the administration (data not shown).

Example 4

Insulin Sensitivity Assay

Figure 2:
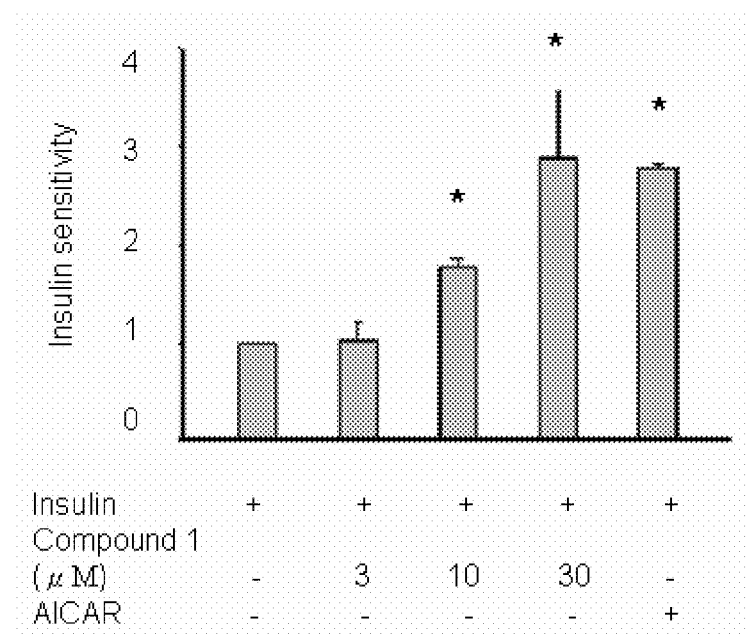
FIG. 2 shows the results of the insulin sensitivity assay in the C2C12 mycrotubes (Example 4) treated with different concentrations of Compound 1. *p<0.05 represent statistical significance compared to the control.

Differentiated $C_2C_{12}$ mycrotubes (American Type Culture Collection: ATCC) were used to conduct an insulin sensitivity assay, which was performed based on the method as described in *Experimental and Molecular Medicine*, Vol. 39, No. 2, 222-229, 2007. Briefly, the cells were incubated with different concentrations of Compound 1 in the presence of insulin 100 nM, and then the glucose uptake was measured. AMPK activator AICAR (5-amino-4-carboxamide imidazole riboside 5'-phosphate, 1 µM) was used as a positive control. FIG. 2 shows the results.

Accordingly, the results described herein indicate that Compound 1 significantly enhanced the insulin sensitivity in the $C_2C_{12}$ mycrotubes. Other pterosin compounds of the invention as listed in Table 1 including Compounds 7, 72, 73, 74 were also confirmed to exhibit the same effect in this assay.

Example 5

Glucose Consumption/Uptake Assay

Figure 3:
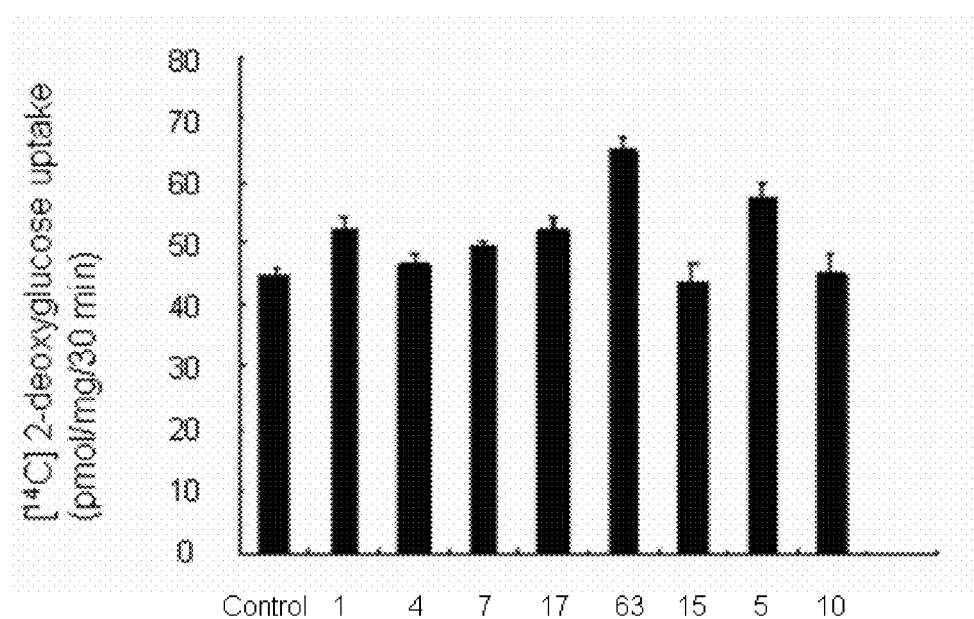
FIG. 3 shows the results of the glucose consumption/uptake assay in the C2C12 mycrotubes treated with different concentrations of Compound 1 (Example 5). *p<0.05 represent statistical significance compared to the control.

Differentiated $C_2C_{12}$ mycrotubes (American Type Culture Collection: ATCC) were used to conduct a glucose consumption/uptake assay, which was performed based on the method as described in *Experimental and Molecular Medicine*, Vol. 39, No. 2, 222-229, 2007. Briefly, the $C_2C_{12}$ cells were pretreated with 0.5 µCi [$^{14}$C]2-DG for 20 min and then incubated with compounds for 1 hour to determine glucose uptake by radio activity. All values are expressed as the means±S.E. of three experiments. FIG. 3 shows the results.

Accordingly, the results described herein indicate that Compound 1 significantly promote glucose consumption/uptake in the $C_2C_{12}$ mycrotubes. Other pterosin compounds of the invention, as listed in Table 1 including Compounds 5, 7, 17, 63, 72, 73, 74 were also confirmed to exhibit the same effect in this assay.

Example 6

Glucose Transporter-4 (Glut4) Expression Assay

Figure 4:
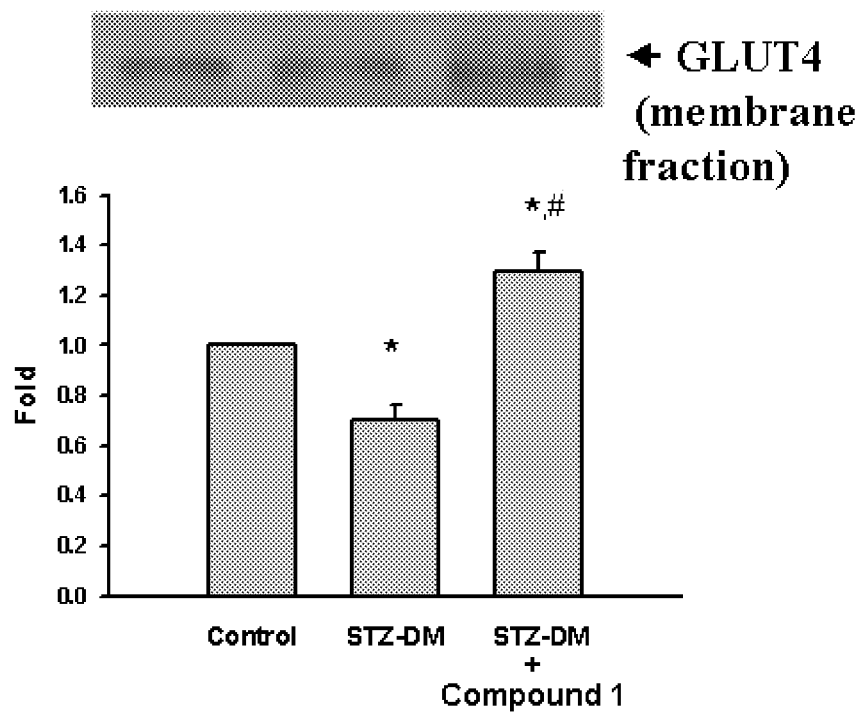
FIG. 4 shows the results of the glucose transporter-4 (Glut4) expression assay in STZ-induced diabetic mice treated with Compound 1 orally (100 mg/kg/day) for 14 days (Example 6). *p<0.05 represent statistical significance compared to the control, and #p<0.05 represent statistical significance compared to STZ-induced diabetic mice.

GLUT4 plays an important role in insulin-induced glucose uptake to maintain normal blood glucose levels. In this study, STZ-induced diabetic mice were treated with Compound 1 orally (100 mg/kg) for 14 days; and then normal mice, STZ-induced diabetic, and the Compound 1-treated STZ-mice as described were analyzed for the Glut4 expression in soleus muscles based on the method as described in *Biochem J.* 1996; 313(Pt 1): 133-140). Briefly, at the end of the experimental period, animals were sacrificed by exsanguinations under diethyl ether anesthesia. Soleus muscles from each animal were excised and weighed. The soleus muscles were homogenized in lysis buffer and centrifugation, and then went to determine the GLUT4 protein expression by western blot analysis. FIG. 4 shows the results.

Accordingly, the results described herein indicate that Compound 1 significantly rescued the redistribution of Glut4 (glucose transporter-4, the insulin-regulated glucose transporter) into the cell membrane of soleus muscles in STZ-induced diabetic mice. Other pterosin compounds of the invention as listed in Table 1 including Compounds 5, 7, 72, 73, 74 were also demonstrated to have the same effect. The results suggest that the pterosin compounds of the invention may activate Glut4 and in turn reduce the blood glucose in diabetic mice.

Example 7

Phosphoenolpyruvate Carboxykinase (PEPCK) Assay

Figure 5:
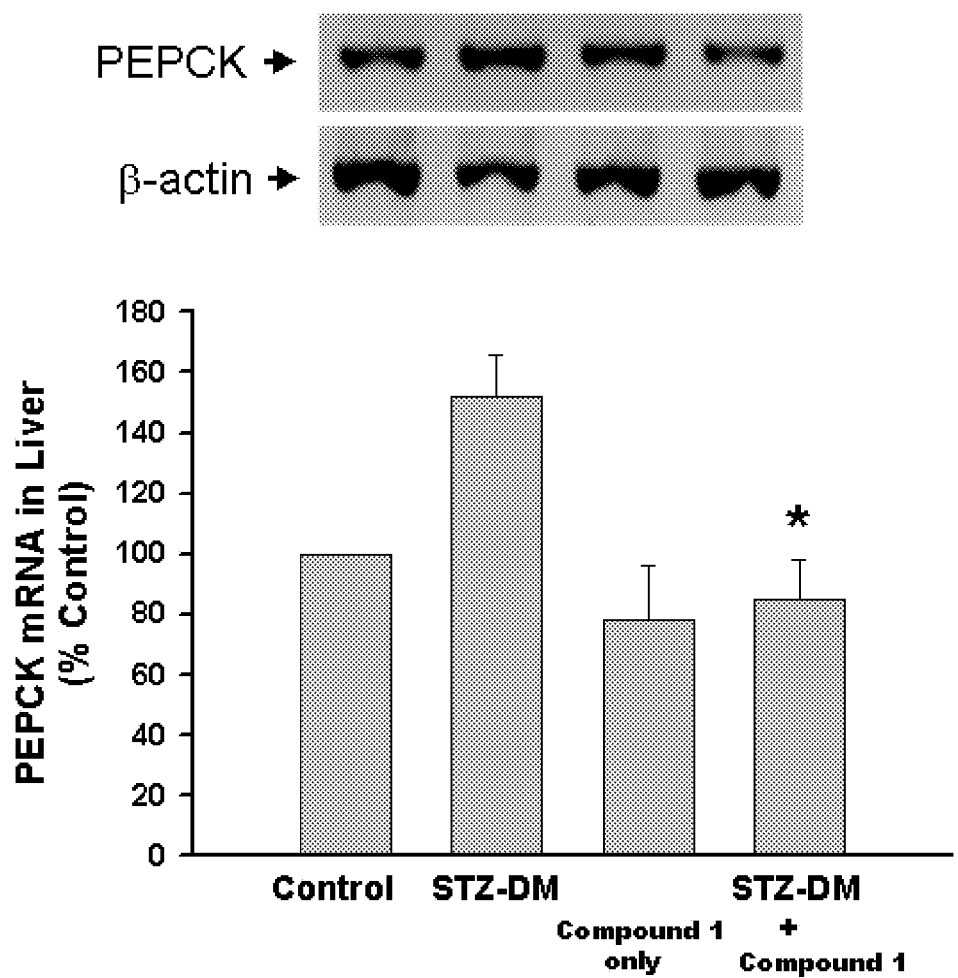
FIG. 5 shows the results of the phosphoenolpyruvate carboxykinase (PEPCK) assay in STZ-induced diabetic mice

PEPCK is known as a key enzyme that controls gluconeogenesis in the liver. In this study, STZ-induced diabetic mice were treated with Compound 1 orally (100 mg/kg) for 14 days, and then normal mice, STZ-induced diabetic, and the Compound 1-treated STZ-mice described above were analyzed for the PEPCK mRNA expression in liver based on the method as described in *Bulletin of Experimental Biology and Medicine* 1979; 87: 568-571. Briefly, at the end of the experimental period, animals were sacrificed by exsanguinations under diethyl ether anesthesia. Livers from each animal were excised and weighed. The liver homogenates were prepared to determine the PEPCK mRNA expression by RT-PCR analysis. FIG. 5 shows the results.

Accordingly, the results described herein indicate that Compound 1 significantly inhibited the overexpression of PEPCK mRNA in the liver of the STZ-induced mice. Other pterosin compounds of the invention listed in Table 1, including Compounds 7 and 73, were also demonstrated to have the same effect.

Example 8

Glucose Tolerance Assay in Type II Diabetic Mice

Figure 6:
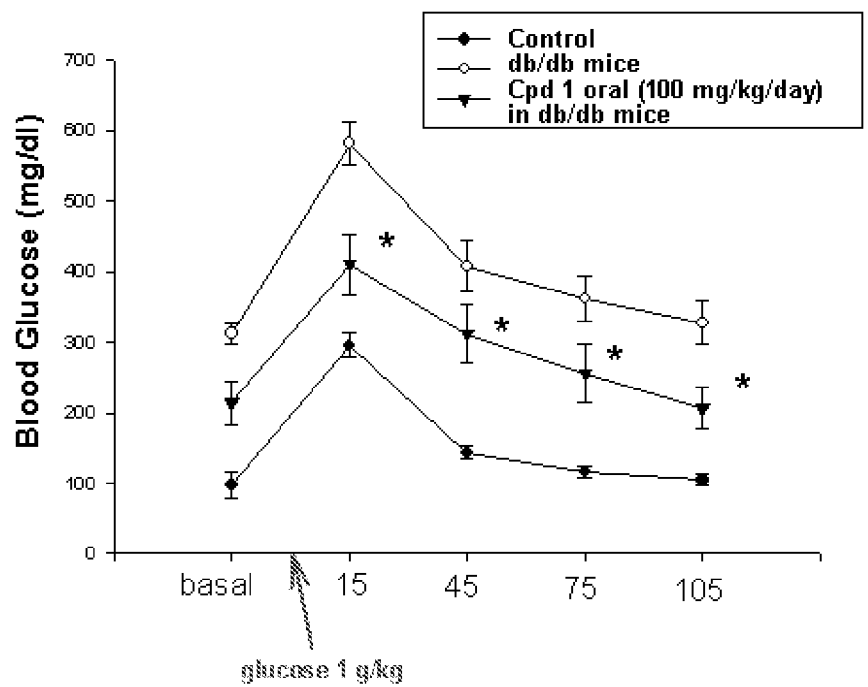
FIG. 6 shows the results of the glucose tolerance assay in db/db mice treated with Compound 1 orally (100 mg/kg/day) for 28 days (Example 8).
Figure 7:
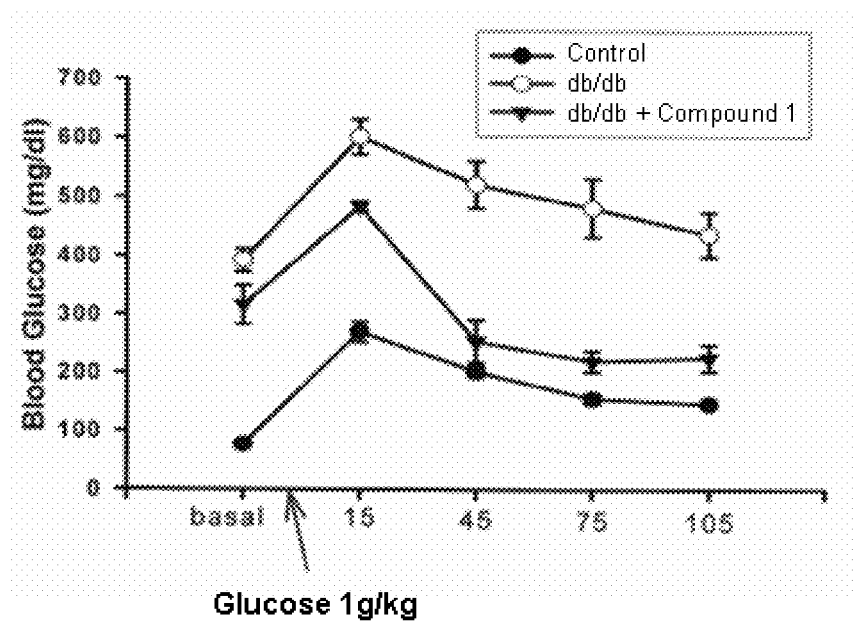
FIG. 7 shows the results of the glucose tolerance assay in db/db mice treated with Compound 1 (30 mg/kg/day) by injection for 21 days (Example 8).
Figure 8:
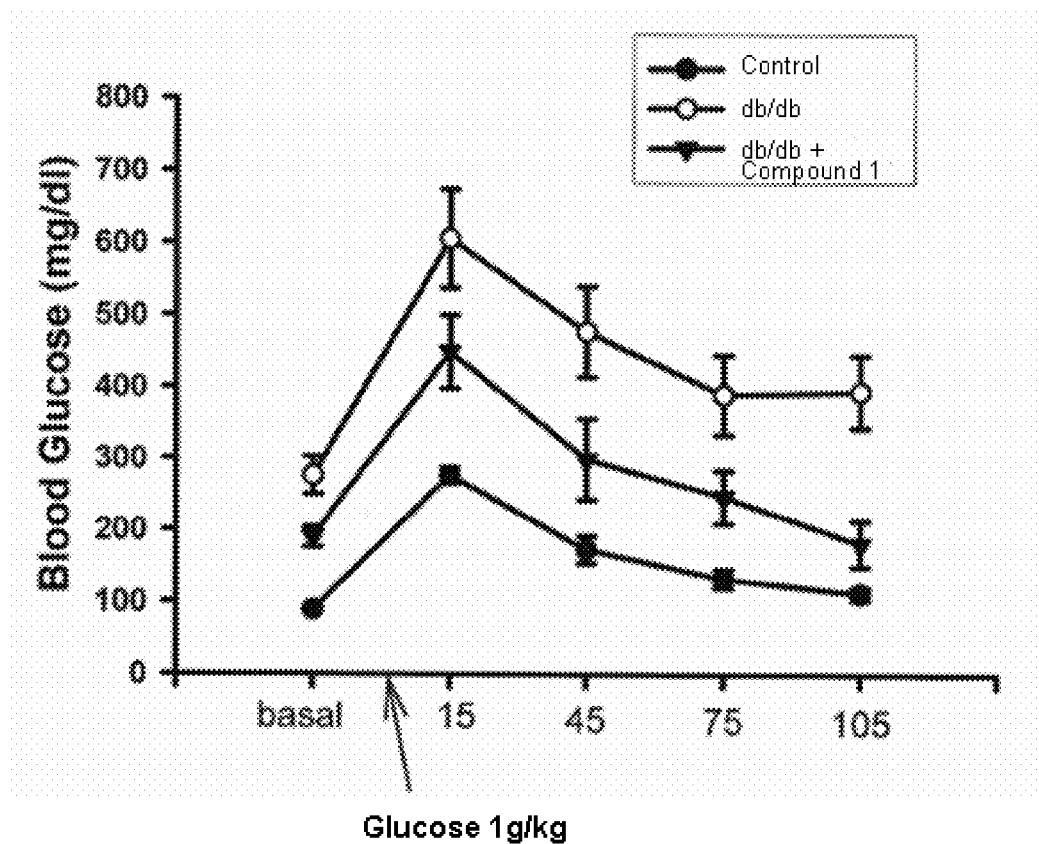
FIG. 8 shows the results of the glucose tolerance assay in db/db mice treated with Compound 1 (30 mg/kg/day) by injection for 28 days (Example 8).

Insulin-resistant C57BL/6J-Leprdb/Lepr$^{db}$ (hereafter, db/db) mice are a well-known mouse model of type II diabetes. See, e.g., *Metabolism*. 2000; 49:22-31). In this study, the db/db mice (Jackson Laboratory) were orally administered with Compound 1 (100 mg/kg/day) for 28 days, or administered with Compound 1 (30 mg/kg/day) via intraperitoneal (i.p.) injection for 21 days or 28 days. Two hours later, normal mice, db/db-mice, and the Compound 1-treated db/db-mice were subjected to a glucose tolerance assay as described in Example 1. FIGS. 6 to 8 show the results.

Results thus obtained indicate that Compound 1 significantly improved the glucose intolerance in db/db-mice.

Example 9

HbA1C (Haemoglobin A1C) Test in Type II Diabetic Mice

In the blood stream, glucose sticks to the haemoglobin to form a "glycosylated haemoglobin" molecule, called haemoglobin A1C or HbA1C. The more glucose in the blood, the more haemoglobin A1C or HbA1C will be present in the blood. The HbA1C test is currently one of the common ways to check if diabetes is under control. See, e.g. *Diabetes Care.* 2001; 24:465-471.

Figure 9:
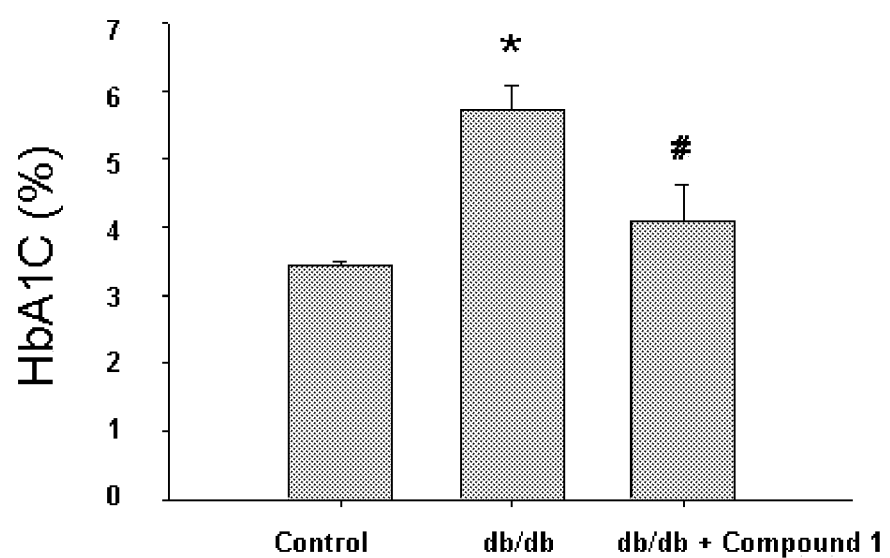
FIG. 9 shows the results of the HbA1C (Haemoglobin A1C) test in STZ-induced diabetic mice treated with Compound 1 orally (100 mg/kg/day) for 28 days (Example 9). *p<0.05 represent statistical significance compared to the control, and #p<0.05 represent statistical significance compared to STZ-induced diabetic mice.

In this study, the db/db mice (Jackson Laboratory) were orally administered with Compound 1 (100 mg/kg/day) for 28 days. Subsequently, normal mice, db/db-mice, and the Compound 1-treated db/db-mice were subjected to a HbA1C test, which was conducted based on a method as described in *Life Sci.* 2005; 77:1391-403. Briefly, at the end of the experimental period, animals were sacrificed by exsanguinations under diethyl ether anesthesia. Plasma was separated from the blood by centrifugation. HbA1c in blood was measured by the standardized method. FIG. 9 shows the results.

Results thus obtained indicate that Compound 1 significantly reduced the HbA1C levels in db/db-mice.

Example 10

HOMA-IR (Homeostasis Model Assessment—Insulin Resistance) Test in Type II Diabetic Mice HOMA-IR is expressed by an empirical mathematical formula based on fasting plasma glucose and fasting plasma insulin levels that was developed as a surrogate measurement of in vivo insulin sensitivity: HOMA value for insulin resistance: (HOMA-IR)=fasting insulin ($\mu$U/ml)×fasting glucose (mmol/l)/22.5. See, e.g., *Biol. Pharm. Bull.* 2007; 30:2196-2200.

Figure 10:
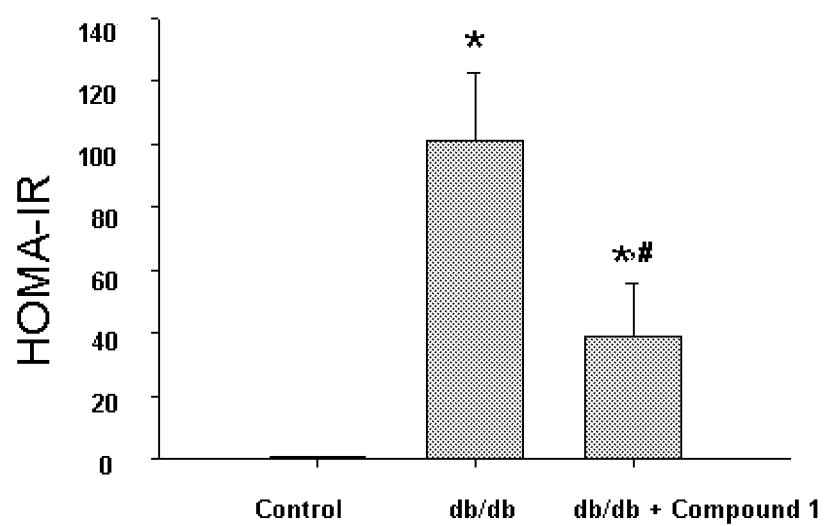
FIG. 10 shows the results of the HOMA-IR (Homeostasis Model Assessment—Insulin Resistance) test in STZ-induced diabetic mice treated with Compound 1 orally (100 mg/kg/day) for 28 days (Example 10). *p<0.05 represent statistical significance compared to the control, and #p<0.05 represent statistical significance compared to STZ-induced diabetic mice.

In this study, the db/db mice (Jackson Laboratory) were orally administered with Compound 1 (100 mg/kg/day) for 28 days. Subsequently, normal mice, db/db-mice, and the Compound 1-treated db/db-mice were subjected to a HOMA-IR test, which was conducted based on a method as described in *Biol. Pharm. Bull.* 2007; 30:2196-2200. Briefly, mouse insulin enzyme immunoassay ELISA kit was used to measure the plasma insulin concentration. Insulin resistance was determined by the homeostasis model assessment (HOMA) method. FIG. 10 shows the results.

Results thus obtained indicate that Compound 1 significantly reduced the HOMA-IR levels in db/db-mice. Other pterosin compounds of the invention listed in Table 1 including Compounds 7 and 73 were also demonstrated to have the same effect in this assay.

Example 11

AMPK Phosphorylation Assay

AMP-activated protein kinase (AMPK) is an important sentinel for energy metabolism, which can be activated by low AMP/ATP ratio, exercise, hypoxia and nutrient starvation. Phosphorylation of $Thr^{172}$ may lead to activation of AMPK, which in turn activates down-stream effectors including acetyl CoA carboxylase, HMG CoA reductase, GLUT-4, glucose-6 phosphatase and PEPCK and regulate fatty acid $\beta$-oxidation, cholesterol synthesis, glucose transport, and gluconeogenesis, respectively. Thus, AMPK may be considered as a molecular target for metabolic syndrome and type II diabetes.

Figure 11:
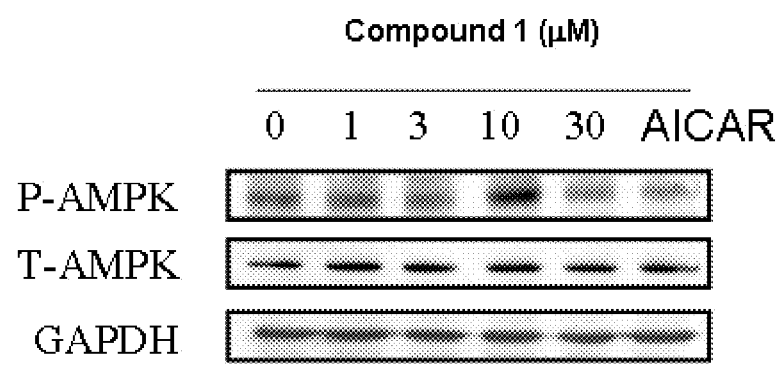
FIG. 11 shows the results of (A) the AMP-activated protein kinase (AMPK) phosphorylation assay and those of (B) the acetyl CoA carboxylase (ACC) phosphorylation assay in the C2C12 mycrotubes (Example 11) treated with different concentrations of Compound 1.
Figure 11:
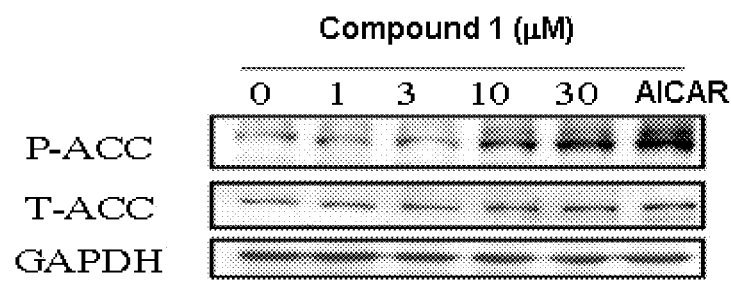

In this study, differentiated C2C12 mycrotubes (American Type Culture Collection: ATCC) were used to conduct an AMPK phosphorylation assay, which was performed based on the method as described in *Experimental and Molecular Medicine*, Vol. 39, No. 2, 222-229, 2007. Briefly, the cells were cultured as in Example 1 and incubated with different concentrations of Compound 1 (0, 1, 3, 10 and 30 $\mu$M) at 37° C. for 1 hour and then cells were lysed. The cell lysate were immunodetected with phosphor-AMPK specific antibody. The equal loading in each lane was demonstrated by the similar intensities of AMPK. AMPK activator AICAR (5-amino-4-carboxamide imidazole riboside 5'-phosphate, 1 mM) was used as a positive control. FIG. 11A shows the results.

Accordingly, the results described herein indicate that incubation of C2C12 myotubes with Compound 1 increased the phosphorylation of the AMPK alpha-subunit at $Thr^{172}$ in a dose dependent manner. Other pterosin compounds of the invention listed in Table 1 including Compounds 1, 4, 7, 52, 72, 73 and 74 were also demonstrated to have the same effect in this assay.

The activation of AMPK by Compound 1 was associated with increased phosphorylation of its downstream substrate, acetyl CoA carboxylase, at $Ser^{79}$ (see FIG. 11B). Phosphorylation and inactivation of acetyl CoA carboxylase may lead to increased fatty acid $\beta$-oxidation.

Taken together, these preliminary results suggest that the compounds of the invention may activate AMPK, which in turn regulate insulin regulation of carbohydrate (see the glucose consumption/uptake assay as described in Example 4) and fatty acid metabolism (see Example 12 below), and can be considered as a potential anti-diabetic and antiobesity agent.

Example 12

Blood Lipid/Cholesterol Assay

Figure 12:
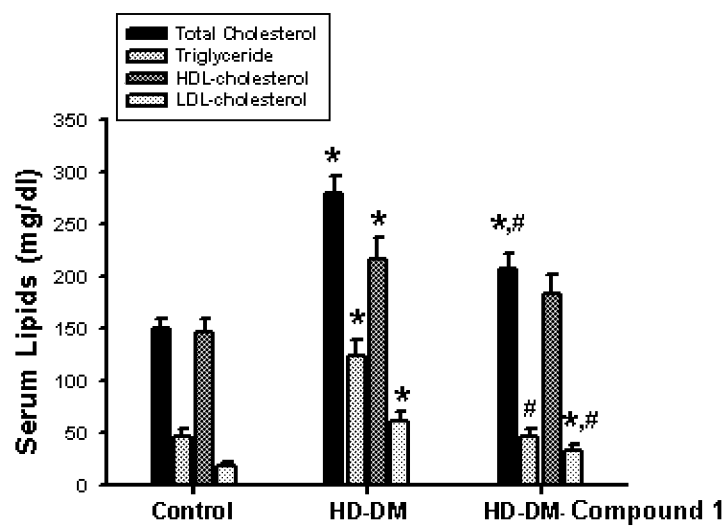
FIG. 12 shows the results of (A) the blood lipid/cholesterol assay in high fat-diet fed (HFD) mice, and (B) the ratios of high-density lipoprotein (HDL)-cholesterol/total cholesterol and low-density lipoprotein (LDL)-cholesterol/total cholesterol. *p<0.05 represent statistical significance compared to the control, and #p<0.05 represent statistical significance compared to HFD mice.
Figure 12:
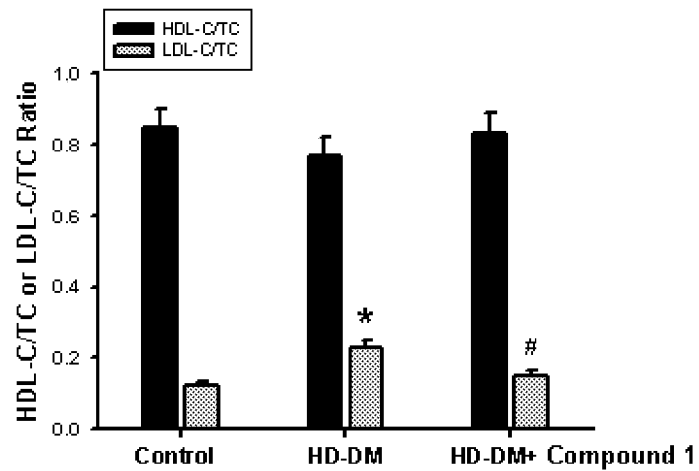

High fat-diet fed (HFD) mice as a type 2 diabetic model were prepared based on the method as previously described in *Diabetes* 53 (Suppl. 3):S215-S219, 2004). In this study, mice were fed with a high-fat diet (TestDiet, Richmond, Ind., USA; fat content 60% kcal) for 8 weeks to induce type 2 diabetes. The HFD mice were treated with Compound 1 orally (100 mg/kg) for 28 days; and then normal mice, HFD mice, and the Compound 1-treated HFD mice were analyzed for the levels of serum lipids, including total cholesterol, triglyceride, high-density lipoprotein (HDL)-cholesterol, and low-density lipoprotein (LDL)-cholesterol by ELISA kits. FIG. 12A shows the results. FIG. 12B shows the ratios of HDL-cholesterol/total cholesterol and LDL-cholesterol/total cholesterol.

Results thus obtained indicate that Compound 1 significantly reduced serum lipids and exhibited anti-obesity effects in HFD mice.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for treating diabetes, comprising administering to a subject in need thereof an effective amount of one or more pterosin compounds selected from the group consisting of Compounds 1-84.

2. The method of claim 1, wherein the diabetes is type I or type II diabetes.

3. The method of claim 1, wherein the pterosin compound(s) is selected from the group consisting of Compounds 1, 4, 5, 7, 10, 12, 15, 17, 28, 63 and 71-75.

4. The method of claim 1, wherein the pterosin compound(s) is administered orally or by injection.

5. The method of claim 1, wherein the pterosin compound(s) is an isolated pterosin compound(s).

6. The method of claim 1, wherein the pterosin compound(s) is formulated to form a pharmaceutical composition.

7. The method of claim 1, wherein the pterosin compound(s) is present in a fern product prepared from Bracken of *Dennstaedtiaceae* or *Pteridaceae*.

8. The method of claim 7, wherein the Bracken is selected from the group consisting of *Dennstaedtia scandens, Histiopteris incisa, Microlepia speluncae, Pteridium aquilinum* var. *latiusculum, Pteridium revolutum, Hypolepis punctata, Ceratopteris thalictroides, Pteris fauriei, Pteris dimidiata,* and *Pteris ensiformis*.

9. A method for treating obesity associated with AMP-activated protein kinase, comprising administering to a subject in need thereof an effective amount of one or more pterosin compounds selected from the group consisting of Compounds 1-84.

10. The method of claim 9, wherein the pterosin compound is selected from the group consisting of Compounds 1, 4, 5, 7, 10, 12, 15, 17, 28, 63 and 71-75.

11. The method of claim 9, wherein the pterosin compound(s) is administered orally or by injection.

12. The method of claim 9, wherein the pterosin compound is an isolated pterosin compound.

13. The method of claim 9, wherein the pterosin compound(s) is formulated to form a pharmaceutical composition.

14. The method of claim 9, wherein the pterosin compound(s) is present in a fern product prepared from Bracken of *Dennstaedtiaceae* or *Pteridaceae*.

15. The method of claim 14, wherein the Bracken is selected from the group consisting of *Dennstaedtia scandens, Histiopteris incisa, Microlepia speluncae, Pteridium aquilinum* var. *latiusculum, Pteridium revolutum, Hypolepis punctata, Ceratopteris thalictroides, Pteris fauriei, Pteris dimidiata,* and *Pteris ensiformis*.

16. The method of claim 9, wherein the amount of the one or more pterosin compounds is effective to reduce the levels of serum lipid or cholesterol in the subject.

17. The method of claim 1, wherein the one or more pterosin compounds are the only active ingredients administered to the subject for treating diabetes.

18. The method of claim 9, wherein the one or more pterosin compounds are the only active ingredients administered to the subject for treating obesity.

* * * * *